(12) United States Patent
Zhao et al.

(10) Patent No.: US 11,767,368 B1
(45) Date of Patent: Sep. 26, 2023

(54) ANTIGEN-BINDING PROTEIN AND USE THEREOF

(71) Applicant: UTC THERAPEUTICS (SHANGHAI) CO., LTD., Shanghai (CN)

(72) Inventors: Yangbing Zhao, Shanghai (CN); Xiaojun Liu, Shanghai (CN); Jie Wang, Shanghai (CN)

(73) Assignee: UTC THERAPEUTICS (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 18/061,533

(22) Filed: Dec. 5, 2022

(30) Foreign Application Priority Data

Jun. 29, 2022 (CN) .......................... 202210750853.1

(51) Int. Cl.
*C07K 16/32* (2006.01)
*A61P 35/00* (2006.01)
*C07K 14/725* (2006.01)

(52) U.S. Cl.
CPC .............. *C07K 16/32* (2013.01); *A61P 35/00* (2018.01); *C07K 14/7051* (2013.01); *C07K 2317/565* (2013.01); *C07K 2317/622* (2013.01); *C07K 2319/02* (2013.01); *C07K 2319/03* (2013.01); *C07K 2319/33* (2013.01)

(58) Field of Classification Search
CPC ............ C07K 16/00–468; C07K 16/32; C07K 14/7051; C07K 2319/00–95
See application file for complete search history.

(56) References Cited

U.S. PATENT DOCUMENTS 8,211,431 B2 * 7/2012 Throsby .................. A61P 43/00
424/165.1
10,174,095 B2 * 1/2019 Brogdon ............ C07K 16/2878
11,197,919 B2 * 12/2021 Priceman ............. C12N 5/0636
2017/0335281 A1 * 11/2017 Loew .............. A61K 39/001156
2020/0399397 A1 * 12/2020 Lee ........................ C07K 16/32

FOREIGN PATENT DOCUMENTS

WO    WO-2015193411 A1 * 12/2015 ............. A61K 35/17

OTHER PUBLICATIONS

Maximiano et al., BioDrugs 30:75-86 (Year: 2016).*
Zhu et al., BBA—Reviews Cancer 1876:188549; doi.org/10.1016/j.bbcan.2021.188549 (Year: 2021).*
Ahmed et al., J Clin Oncol 33(15):1688-96 (Year: 2016).*
Liu et al., Cancer Res 75(17):3596-3607 (Year: 2015).*
Szoor et al., Cancer Letters 484:doi.org/10.1016/j.canlet.2020.04.008 (Year: 2020).*

* cited by examiner

*Primary Examiner* — Jessica H Roark
(74) *Attorney, Agent, or Firm* — Oblon, McClelland, Maier & Neustadt, L.L.P.

(57) ABSTRACT

The present application relates to an antigen-binding protein and use thereof, wherein the antigen-binding protein comprises a VH and a VL, wherein the VH comprises an HCDR1, an HCDR2 and an HCDR3, wherein the HCDR1 comprises an amino acid sequence as set forth in SEQ ID NO: 10, the HCDR2 comprises an amino acid sequence as set forth in SEQ ID NO: 12, the HCDR3 comprises an amino acid sequence as set forth in SEQ ID NO: 14; and the VL comprises an LCDR1, an LCDR2 and an LCDR3, wherein the LCDR1 comprises an amino acid sequence as set forth in SEQ ID NO: 2, the LCDR2 comprises an amino acid sequence as set forth in SEQ ID NO: 4, and the LCDR3 comprises an amino acid sequence as set forth in SEQ ID NO: 6. The present application also relates to a pharmaceutical composition comprising the antigen-binding protein and use thereof for the treatment of a cancer.

28 Claims, 13 Drawing Sheets
Specification includes a Sequence Listing.

ANTIGEN-BINDING PROTEIN AND USE THEREOF

This application claims priority under 35 USC § 119 to CN application No. 202210750853.1 (filed Jun. 29, 2022); the contents of which are incorporated herein by reference.

REFERENCE TO A SEQUENCE LISTING

In accordance with 37 CFR § 1.831, the present specification makes reference to a Sequence Listing submitted electronically as a .xml file named "545448US_ST26". The .xml file was generated on Nov. 29, 2022 and is 41,184 bytes in size. The entire contents of the Sequence Listing are hereby incorporated by reference.

TECHNICAL FIELD

The present application relates to the field of biomedicine, and in particular to an anti-HER2 antigen-binding protein and use thereof.

BACKGROUND

CAR-T cells are used to treat related tumors. T cells can be activated by the binding of chimeric antigen receptors on the T cell surface to specific antigens on the tumor surface, and release various cytokines to kill tumor cells. Proteins, sugars and glycolipids on the surface of tumor cells can be used as potential targets for chimeric antigen receptors, allowing CAR-T to have a wider spectrum of antigens. In addition, the synergistic costimulatory molecules in the CAR structure can increase the proliferation activity and in vivo life period of T cells, and thus enable CAR-T cells to achieve a long-lasting tumor-killing effect.

HER2/neu (ErbB2) gene encodes a 185 kDa transmembrane glycoprotein, which belongs to the epidermal growth factor receptor (EGFR) family. HER2 protein comprises an extracellular domain consisting of 620 amino acid residues, a transmembrane domain consisting of 23 amino acid residues and an intracellular domain with tyrosine kinase activity consisting of 490 amino acid residues (Akiyama T et al., Science, 232 (4758): 1644-1646 (1986)). HER2 (human epidermal growth factor receptor 2) is expressed at a very low level in normal cells, but at a very high level in the embryonic development process, in which it plays an important role in the proliferation, differentiation and migration of cells. Overexpression of HER2 is closely related to the progression of many epithelial cancers, especially in breast cancer and gastric/gastroesophageal junction cancer (GEJ). Current therapies for HER2 are prone to develop drug resistance. Tumors with high HER2 expression have relatively strong metastasis and invasion ability and low sensitivity to chemotherapy, and are prone to recurrence. There is an urgent need for new therapies to meet the needs of patients.

SUMMARY

The present invention aims to overcome the defects of the prior art and provides an anti-HER2 antigen-binding protein, an immunoconjugate, a chimeric antigen receptor comprising an anti-HER2 antigen-binding domain, a coding gene, a construct and use thereof.

In one aspect, the present application provides an isolated antigen-binding protein binding HER2 and comprising an antibody heavy chain variable region (VH), wherein the VH comprises an HCDR1, an HCDR2 and an HCDR3, wherein the HCDR1 comprises an amino acid sequence as set forth in SEQ ID NO: 10, the HCDR2 comprises an amino acid sequence as set forth in SEQ ID NO: 12, and the HCDR3 comprises an amino acid sequence as set forth in SEQ ID NO: 14.

In some embodiments, the isolated antigen-binding protein comprises a VH, wherein the VH comprises framework regions HFR1, HFR2, HFR3 and HFR4, wherein the C-terminus of the HFR1 is directly or indirectly linked to the N-terminus of the HCDR1, the HFR2 is positioned between the HCDR1 and the HCDR2, the HFR3 is positioned between the HCDR2 and the HCDR3, and the N-terminus of the HFR4 is directly or indirectly linked to the C-terminus of the HCDR3; and the HFR1 comprises an amino acid sequence as set forth in SEQ ID NO: 9, the HFR2 comprises an amino acid sequence as set forth in SEQ ID NO: 11, the HFR3 comprises an amino acid sequence as set forth in SEQ ID NO: 13, and the HFR4 comprises an amino acid sequence as set forth in SEQ ID NO: 15.

In some embodiments, the isolated antigen-binding protein comprises a VH, wherein the VH comprises an amino acid sequence as set forth in SEQ ID NO: 22.

In some embodiments, the isolated antigen-binding protein comprises a VL, wherein the VL comprises an LCDR1, an LCDR2 and an LCDR3, wherein the LCDR1 comprises an amino acid sequence as set forth in SEQ ID NO: 2, the LCDR2 comprises an amino acid sequence as set forth in SEQ ID NO: 4, and the LCDR3 comprises an amino acid sequence as set forth in SEQ ID NO: 6.

In some embodiments, the isolated antigen-binding protein comprises a VH and a VL, wherein the VH comprises an HCDR1, an HCDR2 and an HCDR3, wherein the HCDR1 comprises an amino acid sequence as set forth in SEQ ID NO: 10, the HCDR2 comprises an amino acid sequence as set forth in SEQ ID NO: 12, and the HCDR3 comprises an amino acid sequence as set forth in SEQ ID NO: 14; and the VL comprises an LCDR1, an LCDR2 and an LCDR3, wherein the LCDR1 comprises an amino acid sequence as set forth in SEQ ID NO: 2, the LCDR2 comprises an amino acid sequence as set forth in SEQ ID NO: 4, and the LCDR3 comprises an amino acid sequence as set forth in SEQ ID NO: 6.

In some embodiments, the isolated antigen-binding protein comprises a VL, wherein the VL comprises framework regions LFR1, LFR2, LFR3 and LFR4, wherein the C-terminus of the LFR1 is linked directly or indirectly to the N-terminus of the LCDR1, the LFR2 is positioned between the LCDR1 and the LCDR2, the LFR3 is positioned between the LCDR2 and the LCDR3, and the N-terminus of the LFR4 is linked directly or indirectly to the C-terminus of the LCDR3; and the LFR1 comprises an amino acid sequence as set forth in SEQ ID NO: 1, the LFR2 comprises an amino acid sequence as set forth in SEQ ID NO: 3, the LFR3 comprises an amino acid sequence as set forth in SEQ ID NO: 5, and the LFR4 comprises an amino acid sequence as set forth in SEQ ID NO: 7.

In some embodiments, the isolated antigen-binding protein comprises a VL, wherein the VL comprises an amino acid sequence as set forth in SEQ ID NO: 21.

In some embodiments, the isolated antigen-binding protein comprises a VH and a VL, wherein the VH comprises an amino acid sequence as set forth in SEQ ID NO: 22 and the VL comprises an amino acid sequence as set forth in SEQ ID NO: 21.

In some embodiments, wherein the isolated antigen-binding protein comprises an antibody or antigen-binding fragment thereof.

In some embodiments, wherein the antigen-binding fragment includes a Fab, a Fab', a Fv fragment, a F(ab')$_2$, an scFv, a di-scFv, a dAb and/or a VHH.

In some embodiments, wherein the antibody is a chimeric antibody, a humanized antibody or a fully human antibody.

In some embodiments, the isolated antigen-binding protein comprises an antibody heavy chain constant region.

In some embodiments, wherein the antibody heavy chain constant region is derived from a constant region of human IgG.

In some embodiments, the isolated antigen-binding protein comprises an antibody light chain constant region.

In some embodiments, wherein the antibody light chain constant region comprises a human Igκ constant region or a human Igλ constant region.

In some embodiments, the isolated antigen-binding protein includes an scFv, wherein the VH and the VL are linked by a linker.

In some embodiments, wherein the linker includes a peptide linker.

In some embodiments, wherein the linker comprises an amino acid sequence as set forth in SEQ ID NO: 8.

In some embodiments, the isolated antigen-binding protein comprises an amino acid sequence as set forth in SEQ ID NO: 23.

In another aspect, the present application provides an immunoconjugate comprising the isolated antigen-binding protein described herein.

In another aspect, the present application provides a chimeric antigen receptor comprising an extracellular antigen-binding domain, wherein the extracellular antigen-binding domain comprises the isolated antigen-binding protein described herein.

In some embodiments, the chimeric antigen receptor further comprises a transmembrane domain, wherein the transmembrane domain comprises a transmembrane domain derived from one or more proteins selected from the group consisting of: CD8, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4, CD244, FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, SLAM and variants thereof.

In some embodiments, wherein the transmembrane domain comprises a transmembrane domain derived from CD8 or a variant thereof.

In some embodiments, wherein the transmembrane domain comprises an amino acid sequence as set forth in SEQ ID NO: 17.

In some embodiments, the chimeric antigen receptor further comprises an intracellular signaling domain, wherein the intracellular signaling domain comprises an intracellular signaling domain derived from one or more proteins selected from the group consisting of: CD3ζ, CD3δ, CD3γ, CDRε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

In some embodiments, wherein the intracellular signaling domain comprises a signaling domain derived from CD3ζ.

In some embodiments, wherein the intracellular signaling domain comprises an amino acid sequence as set forth in SEQ ID NO: 19.

In some embodiments, wherein the chimeric antigen receptor comprises an extracellular antigen-binding domain, a transmembrane domain, and an intracellular signaling domain.

In some embodiments, wherein the chimeric antigen receptor further comprises an intracellular costimulatory signaling domain, wherein the intracellular costimulatory signaling domain comprises an intracellular costimulatory signaling domain derived from one or more proteins selected from the group consisting of: CD28, 4-1BB (CD137), CD27, CD2, CD7, CD8A, CD8B, OX40, CD226, DR3, SLAM, CDS, ICAM-1, NKG2D, NKG2C, B7-H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, MyD88 and variants thereof.

In some embodiments, wherein the intracellular costimulatory signaling domain is derived from a costimulatory signaling domain of 4-1BB or a variant thereof In some embodiments, wherein the intracellular costimulatory signaling domain comprises an amino acid sequence as set forth in SEQ ID NO: 18.

In some embodiments, the chimeric antigen receptor comprises, from the N-terminus to the C-terminus, an extracellular antigen-binding domain, a transmembrane domain, an intracellular costimulatory signaling domain, and an intracellular signaling domain sequentially.

In some embodiments, wherein the chimeric antigen receptor further comprises a spacer between the transmembrane domain and the extracellular antigen-binding domain, wherein the spacer comprises a hinge region derived from one or more proteins selected from the group consisting of: CD28, CD8, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, LIGHT and variants thereof.

In some embodiments, the spacer comprises a hinge region derived from CD8 or a variant thereof.

In some embodiments, the spacer comprises an amino acid sequence as set forth in SEQ ID NO: 16.

In some embodiments, the chimeric antigen receptor comprises, from the N-terminus to the C-terminus, an extracellular antigen-binding domain, a spacer, a transmembrane domain, an intracellular costimulatory signaling domain, and an intracellular signaling domain sequentially.

In some embodiments, the spacer, transmembrane domain, intracellular costimulatory signaling domain, and intracellular signaling domain of the chimeric antigen receptor comprise, from the N-terminus to the C-terminus, an amino acid sequence as set forth in SEQ ID NO: 24.

In some embodiments, the chimeric antigen receptor further comprises a signal peptide fragment, wherein the C-terminus of the signal peptide fragment is linked to the N-terminus of the extracellular antigen-binding domain.

In some embodiments, the signal peptide fragment includes a CD8 signal peptide fragment.

In some embodiments, the signal peptide fragment comprises an amino acid sequence as set forth in SEQ ID NO: 20.

In some embodiments, the chimeric antigen receptor comprises an amino acid sequence as set forth in SEQ ID NO: 25.

In another aspect, the present application provides an isolated nucleic acid molecule comprising a nucleotide sequence encoding the antigen-binding protein described herein or encoding the chimeric antigen receptor described herein.

In another aspect, the present application provides a construct comprising the nucleic acid molecule described herein.

In another aspect, the present application provides a cell comprising the nucleic acid molecule described herein or the construct described herein, and/or expressing the chimeric antigen receptor described herein.

In some embodiments, wherein the cell includes an immune effector cell.

In some embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell. In some embodiments, wherein the cell includes a CAR-T cell and a CAR-NK cell.

In another aspect, the present application provides a pharmaceutical composition comprising the isolated antigen-binding protein described herein, the immunoconjugate described herein, the chimeric antigen receptor described herein, the nucleic acid molecule described herein, the construct described herein or the cell described herein, and optionally a pharmaceutically acceptable carrier.

In another aspect, the present application provides use of the isolated antigen-binding protein described herein, the immunoconjugate described herein, the chimeric antigen receptor described herein, the nucleic acid molecule described herein, the construct described herein, the cell described herein, or the pharmaceutical composition described herein in preparing a medicament for the prevention and/or treatment of a tumor.

In some embodiments, wherein the tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In some embodiments, wherein the tumor includes an HER2 positive tumor.

In another aspect, the present application provides use of the isolated antigen-binding protein described herein, the immunoconjugate described herein, the chimeric antigen receptor described herein, the nucleic acid molecule described herein, the construct described herein, the cell described herein, or the pharmaceutical composition described herein in preparing a medicament for the prevention and/or treatment of a disease related to abnormal HER2 expression.

In some embodiments, wherein the disease related to abnormal HER2 expression includes a tumor.

In some embodiments, wherein the disease related to abnormal HER2 expression includes an HER2 positive tumor.

In some embodiments, wherein the HER2 positive tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In another aspect, the present application provides a method for preventing and/or treating a tumor, which comprises administering to a subject in need thereof an effective amount of the isolated antigen-binding protein described herein, the immunoconjugate described herein, the chimeric antigen receptor described herein, the nucleic acid molecule described herein, the construct described herein, the cell described herein, or the pharmaceutical composition described herein.

In another aspect, the present application provides a method for preventing and/or treating a disease related to abnormal HER2 expression, which comprises administering to a subject in need thereof an effective amount of the isolated antigen-binding protein described herein, the immunoconjugate described herein, the chimeric antigen receptor described herein, the nucleic acid molecule described herein, the construct described herein, the cell described herein, or the pharmaceutical composition described herein.

In some embodiments, wherein the disease related to abnormal HER2 expression includes a tumor.

In some embodiments, wherein the disease related to abnormal HER2 expression includes an HER2 positive tumor.

In some embodiments, wherein the HER2 positive tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In another aspect, the present application provides a method for detecting HER2 in a biological sample, which comprises making the sample in contact with the antigen-binding protein described herein and detecting a complex, wherein the detecting the complex is indicative of HER2 expression in the sample.

Other aspects and advantages of the present application will be readily apparent to those skilled in the art from the following detailed description. Only exemplary embodiments of the present application have been shown and described in the following detailed description. As those skilled in the art will recognize, the content of the present application enables those skilled in the art to make changes to the specific embodiments disclosed without departing from the spirit and scope of the invention to which the present application pertains. Accordingly, descriptions in the drawings and specification are only illustrative rather than restrictive.

BRIEF DESCRIPTION OF THE DRAWINGS

Specific features of the invention to which the present application pertains are as set forth in appended claims. Features and advantages of the invention to which the present application pertains will be better understood by reference to the exemplary embodiments and drawings described in detail below. The drawings are briefly described as follows.

DETAILED DESCRIPTION

Figure 1:
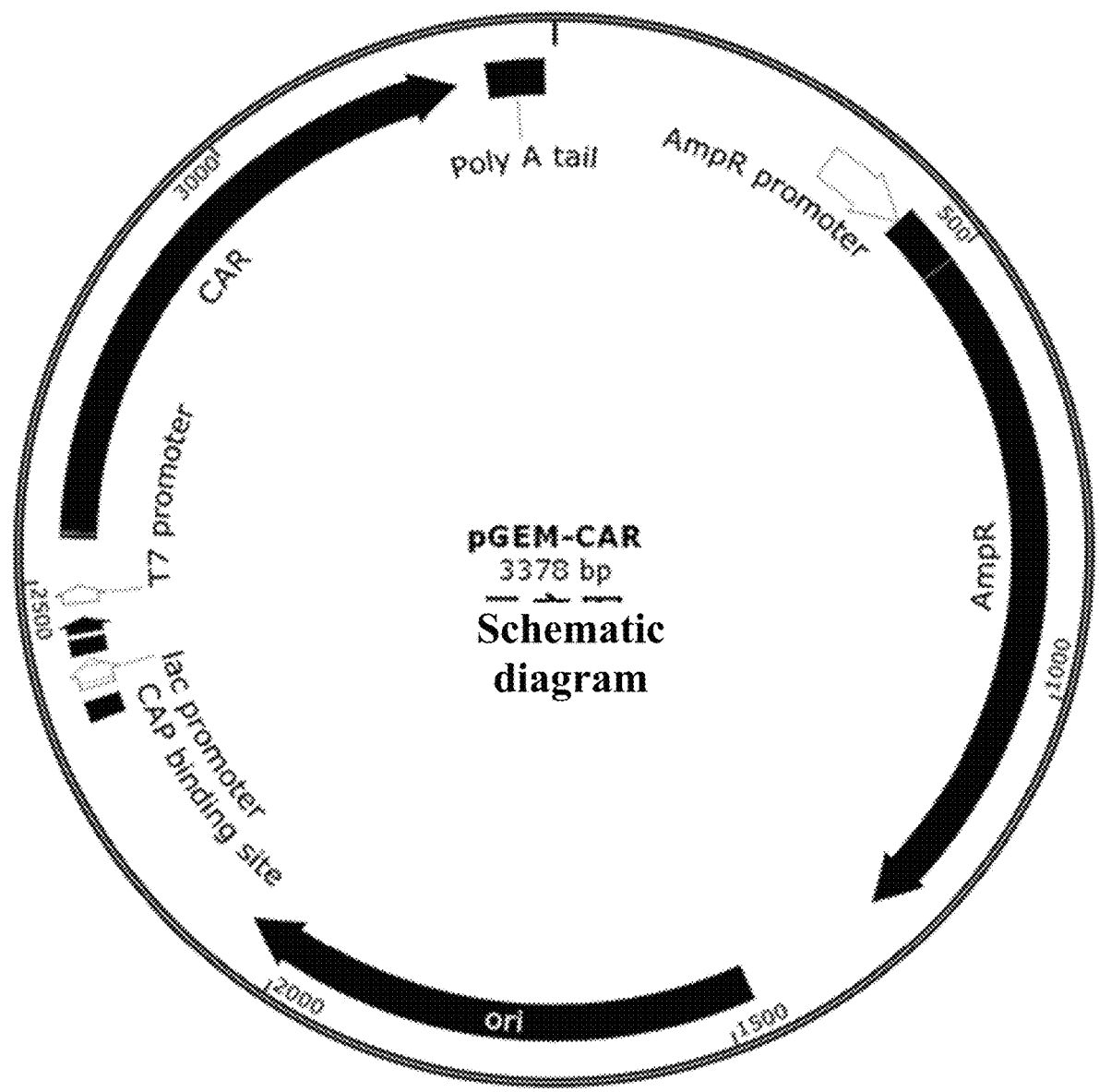
FIG. 1 shows a schematic diagram of a pGEM-CAR vector used in the present application to generate the CAR mRNA.

The embodiments of the present invention are described below with reference to specific examples, and other advantages and effects of the present invention will be readily apparent to those skilled in the art from the disclosure of the present specification.

In the present application, the term "human epidermal growth factor receptor 2 (HER2/ErbB2)", also referred to as HER2/Neu, ErbB-2, CD340 or p185, generally refers to a transmembrane glycoprotein with tyrosine kinase activity, which belongs to the EGFR receptor family. The amino acid sequence of the human HER2 protein can be found under UniProt/Swiss-Prot accession No. P04626. In the present application, the isolated antigen-binding fragment can bind to the HER2 protein. In the present application, the terms "HER2 protein", "HER2 antigen" and "HER2-Fc recombinant protein" are used interchangeably and include any variant or isoform thereof that is naturally expressed by a cell.

In the present application, the term "antibody" is generally used in the broadest sense and specifically encompasses monoclonal antibodies, polyclonal antibodies, dimers, polymers, multispecific antibodies (e.g., bispecific antibodies), and antibody fragments so long as they exhibit the desired biological activity (Miller et al., (2003) Jour. of Immunology 170: 4854-4861). The antibody may be a murine antibody, a human antibody, a humanized antibody or a chimeric antibody, or derived from other species.

A full-length antibody typically refers to an antibody that consists of two "full-length antibody heavy chains" and two "full-length antibody light chains". "Full-length antibody heavy chain" generally refers to a polypeptide consisting of, from the N-terminus to the C-terminus, an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and, in the case of antibodies of the IgE subclass, optionally further comprising an antibody heavy chain constant domain 4 (CH4). In some embodiments, "full-length antibody heavy chain" is a polypeptide consisting of, from the N-terminus to the C-terminus, VH, CH1, HR, CH2 and CH3. "Full-length antibody light chain" is generally a polypeptide consisting of, from the N-terminus to the C-terminus, an antibody light chain variable domain (VL) and an antibody light chain constant domain (CL), abbreviated as VL-CL. The antibody light chain constant domain (CL) may be κ (kappa) or λ (lambda). The two full-length antibody chains are linked together by inter-polypeptide disulfide bonds between the CL domain and the CH1 domain and between the hinge regions of the full-length antibody heavy chains. Examples of typical full-length antibodies are natural antibodies such as IgG (e.g., IgG1 and IgG2), IgM, IgA, IgD, and IgE.

In the present application, the term "antigen-binding fragment" (also referred to herein as a "targeting moiety" or "antigen-binding moiety") generally refers to a portion of an antibody molecule that comprises amino acids responsible for specific binding of an antibody to an antigen. The portion of the antigen specifically recognized and bound by the antibody is referred to as the "epitope" described above. The antigen-binding domain may typically comprise an antibody light chain variable region (VL) and an antibody heavy chain variable region (VH); however, it does not necessarily comprise both. Fd fragment, for example, has two VH regions and typically retains some of the antigen-binding function of the intact antigen-binding domain. Examples of antigen-binding fragments of antibodies include: (1) a Fab fragment, a monovalent fragment having a VL, a VH, a constant light chain (CL) and a CH1 domain; (2) a F(ab')$_2$ fragment, a bivalent fragment having two Fab fragments linked by a disulfide bridge at the hinge region; (3) an Fd fragment, having two VH and CH1 domains; (4) a Fv fragment, having VL and VH domains of a single arm of an antibody; (5) a dAb fragment (Ward et al., "Binding Activities of a Repertoire of Single Immunoglobulin Variable Domains Secreted From Escherichia coli", Nature 341:544-546 (1989), which is incorporated herein by reference in its entirety), having a VH domain; (6) an isolated complementarity determining region (CDR); (7) a single chain Fv (scFv), e.g., derived from an scFV-library. Although the two domains of the Fv fragment, VL and VH, are encoded by separate genes, they may be joined by a recombinant method using a synthetic linker that allows them to be prepared as a single protein chain in which the VL and VH regions pair to form monovalent molecules (referred to as single chain Fv (scFv)) (see, e.g., Huston et al., "Protein Engineering of Antibody Binding Sites: Recovery of Specific Activity in an Anti-Digoxin Single-Chain Fv Analogue Produced in Escherichia coli", Proc. Natl. Acad. Sci. USA 85: 5879-5883 (1988)); and (8) VHH, which relates to variable antigen-binding domains of heavy chain antibodies from Camelidae (camel, dromedary, llama, alpaca, etc.) (see Nguyen V.K. et al., 2000, The EMBO Journal, 19, 921-930; Muylermans S., 2001, J Biotechnol., 74, 277-302 and a review of Vanl and schoot P. et al., 2011, Antiviral Research 92, 389-40). VHH may also be referred to as nanobody (Nb) and/or single domain antibody. Those antibody fragments are obtained using conventional techniques known to those skilled in the art, and assessed for the function in the same manner as for intact antibodies.

In the present application, the term "complementarity determining region" (CDR) generally refers to a complementarity determining region within a variable region of an antigen-binding fragment. In the present application, there are 3 CDRs present in the heavy chain variable region, and the CDRs are named as HCDR1, HCDR2 and HCDR3 for each variable region. The exact boundaries of those CDRs have been defined differently according to different systems. The system described by Kabat (Kabat et al., Sequences of Proteins of Immunological Interest, National Institutes of Health, Bethesda, Md. (1987) and (1991)) provides not only a clear residue numbering system applicable to any variable region of an antigen-binding fragment, but also precise residue boundaries defining 3 CDRs. Those CDRs may be referred to as Kabat CDRs. Chothia and colleagues (Chothia and Lesk, J Mol. Biol., 196: 901-917 (1987) and Chothia et al., Nature 342: 877-883(1989)) found that although there is large diversity at the amino acid level, certain sub-portions within Kabat CDRs take almost identical peptide backbone conformations. Those sub-portions were named as L1, L2 and L3 or H1, H2 and H3, wherein "L" and "H" refer to the light and heavy chain regions, respectively. Those regions may be referred to as Chothia CDRs, which have boundaries that overlap with Kabat CDRs. Other boundaries defining CDRs which overlap with Kabat CDRs have been described by Padlan (FASEB J 9: 133-139 (1995)) and MacCallum (J Mol Biol 262 (5): 732-45 (1996)). In addition, other CDR boundary definitions may not strictly follow one of the above systems, but will nevertheless overlap with Kabat CDRs, although they may be shortened or lengthened according to predictions or experimental findings that a particular residue or a particular group of residues, or even the entire CDRs, do not significantly affect the antigen binding. In the present application, antibody sequences may be divided using the Kabat scheme.

In the present application, the term "FR" generally refers to the more highly conserved portions of antibody variable domains, which are referred to as framework regions. For example, the variable domains of natural heavy and light chains may each comprise four FR regions, namely four in VH (H-FR1, H-FR2, H-FR3 and H-FR4), and four in VL (L-FR1, L-FR2, L-FR3 and L-FR4). "Framework region" generally refers to a portion of the antibody variable region recognized in the art that is present between the more divergent (i.e., hypervariable) CDRs. Such framework regions are typically referred to as frameworks 1 to 4 (FR1, FR2, FR3 and FR4) and provide a framework for presenting six CDRs (three from the heavy chain and three from the light chain) in the three-dimensional space to form an antigen-binding surface.

In the present application, the term "single domain antibody" or "VHH" generally refers to a class of antibodies that lack an antibody light chain, and have only a heavy chain variable region. In certain cases, the single domain antibody may be derived from Bactrian camels, dromedaries, alpacas, llamas, nurse sharks, smooth dogfishes or rays (see, e.g., Kang Xiaozhen et al., *Chinese Journal of Biotechnology*, 2018, 34(12): 1974-1984). For example, the single domain antibody may be derived from alpacas. The single domain antibody may consist of a heavy chain variable region (VH). The term "heavy chain variable region" generally refers to the amino-terminal domain of the heavy chain of an antigen-binding fragment. The heavy chain variable region may be further divided into hypervariable regions termed complementarity determining regions (CDRs), which are scattered over more conserved regions termed framework regions (FRs). Each heavy chain variable region may consist of three CDRs and four FRs arranged from the amino-terminus to the carboxyl-terminus in the following order: FR1, CDR1, FR2, CDR2, FR3, CDR3 and FR4. The heavy chain variable region comprises a binding domain that interacts with an antigen.

In the present application, the term "single chain variable fragment" or "scFv" has its ordinary and conventional meaning, and can include, but is not limited to, for example, a fusion protein comprising the heavy chain (VH) variable region and the light chain (VL) variable region of an immunoglobulin, which are linked to each other with a short linker peptide. Without limitation, the linker may comprise glycine (for flexibility) as well as hydrophilic amino acids (e.g., serine or threonine) (for solubility). The linker may link the N-terminus of VH to the C-terminus of VL, or may link the C-terminus of VH to the N-terminus of VL. In some alternatives, the ligand-binding domain present on the CAR is a single chain variable fragment (scFv). The selection of linker may influence the solubility, expression and correct folding of the scFv. The length of the peptide linker may vary from 10 to 25 amino acids, and generally includes hydrophilic amino acids such as glycine (G) and serine (S). The hydrophilic sequence prevents insertion of the peptide within or between the variable domains throughout the protein folding process. The most commonly used linker is the (Gly4Ser)n motif because of its flexibility, neutral charge and solubility, wherein n is any integer from 1 to 5. It is known that the scFv can become a dimer, a trimer or a tetramer depending on linker length, antibody sequence and other factors (Le Gall F, et al., 1999). Such a form is advantageous and has many possible clinical applications. There is a tandem scFv in the scFv-based bsAb format, which consists of two scFvs connected by a flexible peptide linker, such as a glycine-serine repeat motif in the tandem direction. The well-known bispecific T cell engager (BiTE) technology is based on this format (Chames P. et al., 2009).

In the present application, the term "monoclonal antibody" generally refers to an antibody obtained from a population of substantially homogeneous antibodies, that is, the individual antibodies in the population are identical except for a small amount of natural mutations that may exist. Monoclonal antibodies are generally highly specific for a single antigenic site. Moreover, unlike conventional polyclonal antibody formulations (which generally have different antibodies directed against different determinants), each monoclonal antibody is directed against a single determinant on the antigen. In addition to their specificity, monoclonal antibodies have the advantage that they can be synthesized by hybridoma culture without contamination by other immunoglobulins. The modifier "monoclonal" indicates the characteristic of the antibody obtained from a population of substantially homogeneous antibodies, and is not to be construed as requiring production of the antibody by any particular method. For example, monoclonal antibodies used according to the present application can be prepared in hybridoma cells or can be prepared by the recombinant DNA method.

In the present application, the term "humanized antibody" generally refers to an antibody in which some of or all of the amino acids outside the CDR regions of a non-human antibody (e.g., a mouse antibody) are replaced with corresponding amino acids derived from a human immunoglobulin. In the CDR regions, small additions, deletions, insertions, substitutions or modifications of amino acids may also be permissible, so long as they retain the binding ability of the antibody to a particular antigen. The humanized antibody may optionally comprise at least a portion of a human immunoglobulin constant region. "Humanized antibody" retains antigen specificity similar to the original antibody. "Humanized" forms of non-human (e.g., murine) antibodies may be chimeric antibodies that minimally comprise sequences derived from non-human immunoglobulins. In certain cases, residues in the CDR region of a human immunoglobulin (recipient antibody) can be replaced with residues in the CDR region of a non-human species (donor antibody) such as mouse, rat, rabbit, or non-human primate having the desired properties, affinity and/or ability. In certain cases, residues in the FR region of a human immunoglobulin can be replaced with corresponding non-human residues. In addition, humanized antibodies may comprise amino acid modifications that are not present in the recipient antibody or in the donor antibody. Those modifications may be made to further improve the properties of the antibody, such as binding affinity.

In the present application, the term "fully human antibody" generally refers to an antibody that is expressed by a genetically engineered antibody gene-deleted animal into which a gene that encodes an antibody in human is transferred. All parts of the antibody (including the variable and constant regions of the antibody) are encoded by genes of human origin. The fully human antibody can greatly reduce the immune side effects caused in the human body by the heterologous antibody. Methods for obtaining fully human antibodies in the art can include a phage display technique, a transgenic mice technique, a ribosome display technique, an RNA-peptide technique and the like.

In the present application, the term "immunoconjugate" or "antibody conjugate" generally refers to the linkage of an antibody or an antibody fragment thereof to other active agents, such as chemotherapeutic agents, cytotoxins (cytotoxic agents), immunotherapeutic agents, imaging probes and spectroscopic probes and the like. The linkage may be a covalent bond, or a non-covalent interaction, such as by electrostatic force. A variety of linkers known in the art can be used to form the immunoconjugate. In addition, the immunoconjugate may be provided in the form of a fusion protein that may be expressed from a polynucleotide encoding the immunoconjugate. As used herein, "fusion protein" refers to a protein produced by linking two or more genes or gene fragments that originally encode separate proteins (including peptides and polypeptides). Translation of the fusion gene results in a single protein with functional properties from each of the original proteins.

In the present application, the term "chimeric antigen receptor" or "CAR" generally refers to a group of polypeptides, generally two in the simplest embodiment, which, when in an immune effector cell, provide the cell with specificity for a target cell (usually a cancer cell) and generate intracellular signals. In some embodiments, the CAR comprises at least one extracellular antigen-binding domain (such as VHH, scFv or a portion thereof), a transmembrane domain, and a cytoplasmic signaling domain (also referred to herein as an "intracellular signaling domain") that comprises a functional signaling domain derived from a stimulatory molecule and/or a costimulatory molecule as defined below. In some embodiments, the group of polypeptides are in the same polypeptide chain (e.g., comprise a chimeric fusion protein). In some embodiments, the group of polypeptides are not contiguous with each other, e.g., in different polypeptide chains. In some aspects, the group of polypeptides include a dimerization switch that can couple the polypeptides to each other in the presence of a dimerization molecule, e.g., can couple an antigen-binding domain to an intracellular signaling domain. In one aspect, the stimulatory molecule of the CAR is a ζ chain associated with the T cell receptor complex. In one aspect, the cytoplasmic signaling domain comprises a primary signaling domain (e.g., the primary signaling domain of CD3-ζ. In one aspect, the cytoplasmic signaling domain further comprises one or more functional signaling domains derived from at least one costimulatory molecule as defined below. In one aspect, the costimulatory molecule may be selected from the group consisting of 4-1BB (i.e., CD137), CD27, ICOS and/or CD28. In one aspect, the CAR comprises a chimeric fusion protein, which can comprise an extracellular antigen recognition domain, a transmembrane domain, and an intracellular signaling domain comprising a functional signaling domain derived from a stimulatory molecule. In one aspect, the CAR comprises a chimeric fusion protein, which can comprise an extracellular antigen recognition domain, a transmembrane domain, and an intracellular signaling domain comprising a functional signaling domain derived from a costimulatory molecule and a functional signaling domain derived from a stimulatory molecule. In one aspect, the CAR comprises a chimeric fusion protein, which can comprise an extracellular antigen recognition domain, a transmembrane domain, and an intracellular signaling domain comprising a functional signaling domain derived from one or more costimulatory molecules and a functional signaling domain derived from a stimulatory molecule. In one aspect, the CAR includes a chimeric fusion protein, which can comprise an extracellular antigen recognition domain, a transmembrane domain, and an intracellular signaling domain comprising at least two functional signaling domains derived from one or more costimulatory molecules and a functional signaling domain derived from a stimulatory molecule. In one aspect, the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., VHH) during cell processing and localizes the CAR to the cell membrane.

The CAR of the present application can be configured in a VH-VL or VL-VH configuration with variations in the linker, hinge, transmembrane domain, costimulatory domain and/or transduction domain, and will still retain its efficacy. In some embodiments, the scFv domain present on the CAR is specific for HER2 present on a tumor cell.

The CAR of the present application may comprise linker residues between the various domains added for proper spacing and conformation of the molecule, e.g., a linker comprising an amino acid sequence that links the VH domain and the VL domain and serves the function as a spacer compatible with the interaction of the two sub-binding domains, such that the resulting polypeptide retains specific binding affinity for the same target molecule as an antibody comprising the same light and heavy chain variable regions. The CAR of the present application may comprise one, two, three, four, or five or more linkers. In particular embodiments, the linker has a length of about 1 to about 25 amino acids, about 5 to about 20 amino acids, or about 10 to about 20 amino acids, or any intervening length of amino acids. Illustrative examples of linkers include glycine polymers; glycine-serine polymers; glycine-alanine polymers; alanine-serine polymers; other flexible linkers known in the art, such as a Whitlow linker. Glycine and glycine-serine polymers are relatively unstructured and therefore can act as neutral tethers between domains of a fusion protein (e.g., the CAR of the present application).

In the present application, the term "homology" may generally be equivalent to the sequence "identity". A homologous sequence can include an amino acid sequence that can be at least 80%, 85%, 90%, 99.1%, 99.2%, 99.3%, 99.4%, 99.5%, 99.6%, 99.7%, 99.8%, or 99.9% identical to a subject sequence. Generally, the homologue will comprise the same active site as the subject amino acid sequence, etc. Homology may be considered in terms of similarity (i.e., amino acid residues having similar chemical properties/functions), or may be expressed in terms of sequence identity. In the present application, reference to a sequence having a percent identity of any one of the SEQ ID NOs of an amino acid sequence or a nucleotide sequence refers to a sequence having the percent identity over the entire length of the referenced SEQ ID NO.

To determine sequence identity, sequence alignments can be performed by various means known to those skilled in the art, e.g., using BLAST, BLAST-2, ALIGN, NEEDLE, or Megalign (DNASTAR) software, etc. Those skilled in the art can determine appropriate parameters for alignment, including any algorithms required to achieve optimal alignment over the full length of the sequences being compared.

In the present application, the term "upstream" and "downstream" are defined functionally and generally refer to the orientation or polarity of an encoding nucleotide sequence strand. "Upstream" direction means that the nucleotide is positioned in the 5' direction of a given polynucleotide sequence, i.e., toward the starting nucleotide. In terms of an amino acid sequence, the term "upstream" is interpreted as/refers to the amino acid in the N-terminal direction, i.e., toward the beginning of the polypeptide chain.

In the present application, the term "isolated nucleic acid molecule" generally refers to an isolated form of nucleotides, deoxyribonucleotides or ribonucleotides or analogs thereof of any length, isolated from their natural environment, or artificially synthesized. The term "nucleic acid" or "polynucleotide" or "nucleic acid molecule" generally refers to deoxyribonucleic acid (DNA) or ribonucleic acid (RNA) and polymers thereof in either single- or double-stranded form. Unless specifically limited, the term can include nucleic acids comprising analogs of natural nucleotides that have similar binding properties as the reference nucleic acid (e.g., with sequence information shown) and are metabolized in a manner similar to naturally occurring nucleotides. Unless otherwise indicated, the sequence of a nucleic acid may include conservatively modified variants thereof (e.g., degenerate codon substitutions), alleles, orthologs, SNPs, and complementary sequences, as well as the sequences explicitly indicated.

In the present application, the term "construct" generally refers to a nucleic acid molecule capable of self-replicating in a suitable host, which transfers an inserted nucleic acid molecule into a host cell and/or between host cells. The construct may include vectors primarily for the insertion of DNA or RNA into a cell, vectors primarily for the replication of DNA or RNA, and vectors primarily for the expression of transcription and/or translation of DNA or RNA. The vector also includes vectors having a variety of the above-described functions. The construct may be a polynucleotide capable of being transcribed and translated into a polypeptide when introduced into a suitable host cell. Typically, the vector can produce the desired expression product by culturing an appropriate host cell containing the vector. The term "construct" includes vectors (e.g., plasmids, phages, phasmids, viruses, cosmids, F-cosmids, or other purified nucleic acid vectors) that can be altered, modified, or engineered to contain more, less, or different nucleic acid sequences than those included in the native or natural nucleic acid molecule from which the vectors are derived.

In the present application, the term "cell" generally refers to an individual cell, cell line or cell culture that may contain or has contained a vector comprising the isolated nucleic acid molecule described herein, or that is capable of expressing the isolated antigen-binding fragment described herein. The host cell may comprise progeny of a single host cell. Due to natural, accidental or deliberate mutations, progeny cells may not necessarily be identical in morphology or in genome to the original parent cell, but is capable of expressing the isolated antigen-binding fragment described herein. The host cell may be obtained by transfecting cells with the vector described herein in vitro. The host cell may be a prokaryotic cell (e.g., *E. coli*) or a eukaryotic cell (e.g., a yeast cell, or a COS cell, a Chinese hamster ovary (CHO) cell, a HeLa cell, an HEK293 cell, a COS-1 cell, an NSO cell, or a myeloma cell). For example, the host cell may be an *E. coli* cell. For example, the host cell may be a yeast cell. For example, the host cell may be a mammalian cell. For example, the mammalian cell may be a CHO-K1 cell.

In the present application, the term "immune effector cell" generally refers to an immune cell involved in an immune response for performing an effector function. For example, the performing an effector function may include clearing foreign antigens, promoting an immune effector response, or the like. The immune effector cell may include plasma cells, T cells, B cells, natural killer (NK) cells, natural killer T (NKT) cells, mast cells, and myeloid-derived phagocytes.

The immune effector cell of the present application may be autologous/autogeneic ("self") or non-autologous ("non-self", e.g., allogeneic, syngeneic or xenogeneic). In the present application, the term "autologous" generally refers to cells from the same subject. "Allogeneic" generally means that cells are of the same species as but genetically different from the cells to which they are compared. "Syngeneic" generally means that cells are from different subjects but genetically identical to the cells to which they are compared. "Xenogeneic" generally means that cells are of different species from the cell to which they are compared. In some embodiments, the cells of the present application are autologous or allogeneic.

In the present application, the term "T cell" or "T lymphocyte" may be any T cells, such as cultured T cells, e.g., primary T cells, or T cells from a cultured T cell line, e.g., Jurkat, SupTI, etc., or T cells obtained from a mammal (preferably a primate, species including monkey, dog or human). If obtained from a mammal, the T cells may be obtained from a number of sources including, but not limited to, blood, bone marrow, lymph nodes, thymus, or other tissues or fluids. The T cell may also be enriched or purified. The T cell may be obtained by maturing a hematopoietic stem cell into a T cell in vitro or in vivo. In exemplary aspects, the T cell is a human T cell. In exemplary aspects, the T cell is a T cell isolated from a human. The T cell may be any type of T cells, including NKT cells, and may have any developmental stage, including but not limited to $CD4^+$/$CD8^+$ double positive T cells; $CDA^+$ helper T cells; e.g., Th1 and Th2 cells, $CD8^+$ T cells (e.g., cytotoxic T cells); peripheral blood mononuclear cells (PBMCs); peripheral blood leukocytes (PBLs); tumor infiltrating cells (TILs); memory T cells; untreated T cells, and the like. Preferably, the T cell is a $CD8^+$ T cell or a $CD4^+$ T cell. In some alternatives, the T cell is allogeneic (from different donors of the same species) to the recipient subject that receives the cell or cell to be received (e.g., the cells are in the form of a therapeutic composition); in some alternatives, the T cell is autologous (the donor and recipient are the same); in some alternatives, the T cell is syngeneic (the donor and recipient are different, but are homozygotic twins).

In the present application, the term "expression" generally refers to the transcription and/or translation of a particular nucleotide sequence.

In the present application, the terms "tumor" and "cancer" are used interchangeably and generally refer to a disease characterized by rapid and uncontrolled growth of abnormal cells. Cancer cells can spread to other parts of the body locally or through the bloodstream and lymphatic system. Examples of various cancers are described herein and include, but are not limited to, breast cancer, prostate cancer, ovarian cancer, cervical cancer, skin cancer, pancreatic cancer, colorectal cancer, kidney cancer, liver cancer, brain cancer, lymphoma, leukemia, lung cancer, and the like. The term "cancer" or "tumor" includes premalignant and malignant cancers and tumors, and also encompasses solid tumors and non-solid tumors.

In the present application, the term "preventing and/or treating" includes not only preventing and/or treating the disease, but also generally preventing the onset of the disease; slowing or reversing the progression of the disease; preventing or slowing the onset of one or more symptoms associated with the disease; reducing and/or alleviating one or more symptoms associated with the disease; reducing the severity and/or duration of the disease and/or any symptoms associated with the disease and/or preventing further increases in the severity of the disease and/or any symptoms associated with the disease; preventing, reducing or reversing any physiological damage caused by the disease; and any pharmacological effect which would normally be beneficial to the patient being treated. The composition of the present application forms a viable therapeutic agent that does not need to achieve a complete cure or eradication of any symptom or manifestation of the disease. As recognized in the related art, the drug used as a therapeutic agent can reduce the severity of a given disease state, but does not need to eliminate every manifestation of the disease to be considered a useful therapeutic agent. Similarly, a prophylactically administered treatment constitutes a viable prophylactic agent that does not need to be entirely effective in preventing the onset of the condition. It is sufficient to simply reduce the impact of the disease (e.g., by reducing the number or severity of its symptoms, or by increasing the effectiveness of another treatment, or by producing another beneficial effect), or reduce the likelihood of the disease developing or worsening, in the subject.

In the present application, the term "administering" generally refers to the delivery of proteins (including immunoglobulins) to a human or animal in need thereof by any route known in the art. Pharmaceutically acceptable carriers and formulations or compositions are also well known in the art. Routes of administration may include: intravenous, intramuscular, intradermal, subcutaneous, transdermal, mucosal, intratumoral, or mucosal administrations. Alternatively, the term may refer to the delivery of a vector for recombinant protein expression to a cell or cultured cell and/or a cell or organ of a subject. Such administration or introduction may occur in vivo, in vitro, or in vitro followed by in vivo. The vector for recombinant protein or polypeptide expression may be introduced into cells by: transfection, which generally refers to the insertion of heterologous DNA into a cell by physical means (e.g., calcium phosphate transfection, electroporation, microinjection, or lipofection); infection, which generally refers to the introduction of an infectious agent (i.e., a virus); or transduction, which generally refers to stable infection of a cell by a virus, or transfer of genetic material from one microorganism to another by a viral agent (e.g., a phage).

In the present application, the term "pharmaceutically acceptable" generally refers to those compounds, materials, compositions, and/or dosage forms which are, commensurate with a reasonable benefit/risk ratio, suitable, within the scope of sound medical judgment, for use in contact with the tissues of human beings and animals without excessive toxicity, irritation, allergic response, or other problems or complications.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants compatible with pharmaceutical administration, glidants, pH adjusting agents, buffering agents, enhancers, wetting agents, solubilizers, and the like. The use of such media and agents for pharmaceutically active substances is well known in the art. The composition may contain an additional active compound that provides supplemental, additional or enhanced therapeutic functions.

In the present application, the term "effective amount" or "effective dose" generally refers to an amount sufficient to achieve, or at least partially achieve, a desired effect. "Therapeutically effective amount" or "therapeutically effective dose" of a drug or therapeutic agent is generally any amount of drug that promotes the regression of a disease (as evidenced by a decrease in the severity of symptoms of the disease, an increase in the frequency and duration of the asymptomatic phase of the disease, or the prevention of damage or disability due to the development of the disease) when used alone or in combination with another therapeutic agent.

In the present application, the term "comprising" generally means including, summarizing, containing or encompassing. In some cases, the term also means "being" or "consisting of...".

The term "about" generally means varying by 0.5%-40% above or below the stated value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below the stated value.

In the present application, the term "subject" generally refers to a human or non-human animal, including but not limited to cat, dog, horse, pig, cow, sheep, rabbit, mouse, rat, monkey, etc.

In one aspect, the present application provides an isolated antigen-binding protein targeting HER2, which comprises a VH, wherein the VH comprises an HCDR1, an HCDR2 and an HCDR3, wherein the HCDR1 comprises an amino acid sequence as set forth in SEQ ID NO: 10 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 10, the HCDR2 comprises an amino acid sequence as set forth in SEQ ID NO: 12 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 12, and the HCDR3 comprises an amino acid sequence as set forth in SEQ ID NO: 14 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 14.

In some embodiments, the isolated antigen-binding protein comprises a VH, wherein the VH comprises the framework regions HFR1, HFR2, HFR3, and HFR4, the C-terminus of the HFR1 is directly or indirectly linked to the N-terminus of the HCDR1, the HFR2 is positioned between the HCDR1 and the HCDR2, the HFR3 is positioned between the HCDR2 and the HCDR3, and the N-terminus of the HFR4 is directly or indirectly linked to the C-terminus of the HCDR3; wherein the HFR1 comprises the amino acid sequence as set forth in SEQ ID NO: 9 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 9, the HFR2 comprises the amino acid sequence as set forth in SEQ ID NO: 11 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 11, the HFR3 comprises the amino acid sequence as set forth in SEQ ID NO: 13 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 13, and HFR4 comprises the amino acid sequence as set forth in SEQ ID NO: 15 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 15.

For example, the isolated antigen-binding protein comprises a VH, wherein the VH may comprise, from the N-terminus to the C-terminus, HFR1-HCDR1-HFR2-HCDR2-HFR3-HCDR3-HFR4 sequentially, wherein the HCDR1 comprises an amino acid sequence as set forth in SEQ ID NO: 10, the HCDR2 comprises an amino acid sequence as set forth in SEQ ID NO: 12, the HCDR3 comprises an amino acid sequence as set forth in SEQ ID NO: 14, the HFR1 comprises an amino acid sequence as set forth in SEQ ID NO: 9, the HFR2 comprises an amino acid sequence as set forth in SEQ ID NO: 11, the HFR3 comprises an amino acid sequence as set forth in SEQ ID NO: 13, and the HFR4 comprises an amino acid sequence as set forth in SEQ ID NO: 15.

For another example, the isolated antigen-binding protein comprises a VH, wherein the VH may comprise an amino acid sequence as set forth in SEQ ID NO: 22 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 22.

In some embodiments, the isolated antigen-binding protein comprises a VL, wherein the VL comprises an LCDR1, an LCDR2 and an LCDR3, wherein the LCDR1 comprises an amino acid sequence as set forth in SEQ ID NO: 2 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 2; the LCDR2 comprises an amino acid sequence as set forth in SEQ ID NO: 4 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 4; and the LCDR3 comprises an amino acid sequence as set forth in SEQ ID NO: 6 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 6.

In some embodiments, the isolated antigen-binding protein comprises a VH and a VL, wherein the VH comprises an HCDR1, an HCDR2 and an HCDR3, wherein the HCDR1 comprises an amino acid sequence as set forth in SEQ ID NO: 10 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 10, the HCDR2 comprises an amino acid sequence as set forth in SEQ ID NO: 12 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 12, and the HCDR3 comprises an amino acid sequence as set forth in SEQ ID NO: 14 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 14; and the VL comprises an LCDR1, an LCDR2 and an LCDR3, wherein the LCDR1 comprises an amino acid sequence as set forth in SEQ ID NO: 2 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 2, the LCDR2 comprises an amino acid sequence as set forth in SEQ ID NO: 4 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 4, and the LCDR3 comprises an amino acid sequence as set forth in SEQ ID NO: 6 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 6.

For example, the isolated antigen-binding protein comprises a VH and a VL, wherein the VH comprises an HCDR1, an HCDR2 and an HCDR3, wherein the HCDR1 may comprise an amino acid sequence as set forth in SEQ ID NO: 10, the HCDR2 may comprise an amino acid sequence as set forth in SEQ ID NO: 12, and the HCDR3 may comprise an amino acid sequence as set forth in SEQ ID NO: 14; and the VL comprises an LCDR1, an LCDR2 and an LCDR3, wherein the LCDR1 may comprise an amino acid sequence as set forth in SEQ ID NO: 2, the LCDR2 may comprise an amino acid sequence as set forth in SEQ ID NO: 4, and the LCDR3 may comprise an amino acid sequence as set forth in SEQ ID NO: 6.

In some embodiments, the isolated antigen-binding protein comprises a VL, wherein the VL comprises framework regions LFR1, LFR2, LFR3 and LFR4, wherein the LFR1 is directly or indirectly linked to the N-terminus of the LCDR1, the LFR2 is positioned between the LCDR1 and the LCDR2, the LFR3 is positioned between the LCDR2 and the LCDR3, the N-terminus of the LFR4 is directly or indirectly linked to the C-terminus of the LCDR3; wherein the LFR1 comprises an amino acid sequence as set forth in SEQ ID NO: 1 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 1; the LFR2 comprises an amino acid sequence as set forth in SEQ ID NO: 3 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 3; the LFR3 comprises an amino acid sequence as set forth in SEQ ID NO: 5 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 5, and the LFR4 comprises an amino acid sequence as set forth in SEQ ID NO: 7 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 7.

For example, the isolated antigen-binding protein comprises a VL, wherein the VL may comprise, from the N-terminus to the C-terminus, LFR1-LCDR1-LFR2-LCDR2-LFR3-LCDR3-LFR4 sequentially; wherein the VL comprises an LCDR1, an LCDR2 and an LCDR3, wherein the LCDR1 comprises an amino acid sequence as set forth in SEQ ID NO: 2, the LCDR2 comprises an amino acid sequence as set forth in SEQ ID NO: 4, the LCDR3 comprises an amino acid sequence as set forth in SEQ ID NO: 6, the LFR1 comprises an amino acid sequence as set forth in SEQ ID NO: 1, the LFR2 comprises an amino acid sequence as set forth in SEQ ID NO: 3, the LFR3 comprises an amino acid sequence as set forth in SEQ ID NO: 5, and the LFR4 comprises an amino acid sequence as set forth in SEQ ID NO: 7.

For another example, the isolated antigen-binding protein comprises a VL, wherein the VL may comprise an amino acid sequence as set forth in SEQ ID NO: 21 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 21.

For another example, the isolated antigen-binding protein comprises a VH and a VL, wherein the VH may comprise an amino acid sequence as set forth in SEQ ID NO: 22 and the VL may comprise an amino acid sequence as set forth in SEQ ID NO: 21.

In some embodiments, the isolated antigen-binding protein comprises an antibody or an antigen-binding fragment thereof.

For example, the antigen-binding fragment may comprise a Fab, a Fab', a Fv fragment, a F(ab')$_2$, an scFv, a di-scFv, a dAb and/or a VHH.

In some embodiments, wherein the antibody may include a monoclonal antibody, a polyclonal antibody (e.g., a biclonal antibody), a chimeric antibody, a humanized antibody, or a fully human antibody.

In some embodiments, the isolated antigen-binding protein comprises an antibody heavy chain constant region.

In some embodiments, wherein the antibody heavy chain constant region is derived from a constant region of human IgG.

For example, the antibody heavy chain constant region is derived from a constant region of human IgG1, IgG2, IgG3 or IgG4. For example, the isolated antigen-binding protein may comprise an antibody heavy chain comprising an antibody heavy chain variable region and an antibody heavy chain constant region, wherein the antibody heavy chain variable region may comprise an amino acid sequence as set forth in SEQ ID NO: 22, and the antibody heavy chain constant region is derived from a constant region of human IgG1.

In some embodiments, the isolated antigen-binding protein comprises an antibody light chain constant region.

In some embodiments, wherein the antibody light chain constant region comprises a human Igκ constant region or a human Igλ constant region.

For example, the isolated antigen-binding protein may comprise an antibody light chain comprising an antibody light chain variable region and an antibody light chain constant region, wherein the antibody light chain variable region comprises an amino acid sequence as set forth in SEQ ID NO: 21, and the antibody light chain constant region is derived from a human IgK constant region.

For another example, the isolated antigen-binding protein may comprise an antibody heavy chain and an antibody light chain, wherein the antibody heavy chain comprises an antibody heavy chain variable region and an antibody heavy chain constant region, wherein the antibody heavy chain variable region may comprises an amino acid sequence as set forth in SEQ ID NO: 22, and the antibody heavy chain constant region is derived from a constant region of human IgG1; the antibody light chain comprises an antibody light chain variable region and an antibody light chain constant region, wherein the antibody light chain variable region may comprise an amino acid sequence as set forth in SEQ ID NO: 21, and the antibody light chain constant region is derived from a human Igκ constant region.

In some embodiments, the isolated antigen-binding protein includes an scFv, wherein the VH and VL are linked by a linker.

In some embodiments, wherein the linker includes a peptide linker.

In some embodiments, wherein the linker comprises an amino acid sequence as set forth in SEQ ID NO: 8.

In some embodiments, the scFv includes VH-linker-VL or VL-linker-VH.

For example, the scFv includes VH-linker-VL or VL-linker-VH; wherein the VH may comprise an amino acid sequence as set forth in SEQ ID NO: 22, and the VL may comprise an amino acid sequence as set forth in SEQ ID NO: 21.

For another example, the isolated antigen-binding protein may comprise an amino acid sequence as set forth in SEQ ID NO: 23 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 23.

In another aspect, the present application provides an isolated polypeptide comprising the isolated antigen-binding protein described herein.

In another aspect, the present application provides an immunoconjugate comprising the isolated antigen-binding protein described herein.

In some embodiments, the isolated antigen-binding protein is linked to an additional active agent. Without limitation, the additional active agent may include chemotherapeutic agents, cytotoxins (cytotoxic agents), immunotherapeutic agents, imaging probes or spectroscopic probes.

For example, the immunoconjugate may be an antibody-drug conjugate (ADC), wherein the antibody is conjugated to one or more drugs.

In another aspect, the present application provides a chimeric antigen receptor targeting HER2, which comprises an extracellular antigen-binding domain, wherein the extracellular antigen-binding domain comprises the isolated antigen-binding protein described herein.

For example, the extracellular antigen-binding domain may comprise a VH, wherein the VH comprises an HCDR1, an HCDR2 and an HCDR3, wherein the HCDR1 comprises an amino acid sequence as set forth in SEQ ID NO: 10, the HCDR2 comprises an amino acid sequence as set forth in SEQ ID NO: 12, and the HCDR3 comprises an amino acid sequence as set forth in SEQ ID NO: 14.

For another example, the extracellular antigen-binding domain may comprise a VH, wherein the VH may comprise an amino acid sequence as set forth in SEQ ID NO: 22 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 22.

For another example, the extracellular antigen-binding domain may comprise a VH and a VL, wherein the VH comprises an HCDR1, an HCDR2 and an HCDR3,wherein the HCDR1 may comprise an amino acid sequence as set forth in SEQ ID NO: 10, the HCDR2 may comprise an amino acid sequence as set forth in SEQ ID NO: 12, and the HCDR3 may comprise an amino acid sequence as set forth in SEQ ID NO: 14; and the VL comprises an LCDR1, an LCDR2 and an LCDR3, wherein the LCDR1 may comprise an amino acid sequence as set forth in SEQ ID NO: 2, the LCDR2 may comprise an amino acid sequence as set forth in SEQ ID NO: 4, and the LCDR3 may comprise an amino acid sequence as set forth in SEQ ID NO: 6.

For another example, the extracellular antigen-binding domain may comprise a VH and a VL, wherein the VH may comprise an amino acid sequence as set forth in SEQ ID NO: 22, and the VL may comprise an amino acid sequence as set forth in SEQ ID NO: 21.

In some embodiments, wherein the extracellular antigen-binding domain includes a full-length antibody, a Fab, a single chain variable fragment (scFv), or a single domain antibody (VHH). For example, the extracellular antigen-binding domain includes an scFv.

For example, the extracellular antigen-binding domain includes an scFv comprising a VH and a VL, wherein the VH comprises an HCDR1, an HCDR2 and an HCDR3, wherein the HCDR1 may comprise an amino acid sequence as set forth in SEQ ID NO: 10, the HCDR2 may comprise an amino acid sequence as set forth in SEQ ID NO: 12, and the HCDR3 may comprise an amino acid sequence as set forth in SEQ ID NO: 14; and the VL comprises an LCDR1, an LCDR2 and an LCDR3, wherein the LCDR1 may comprise an amino acid sequence as set forth in SEQ ID NO: 2, the LCDR2 may comprise an amino acid sequence as set forth in SEQ ID NO: 4, and the LCDR3 may comprise an amino acid sequence as set forth in SEQ ID NO: 6.

In some embodiments, the chimeric antigen receptor further comprises a transmembrane domain, wherein the transmembrane domain comprises a transmembrane domain derived from one or more proteins selected from the group consisting of: CD8, CD28, CD3ε (CD3e), 4-1BB, CD4, CD27, CD7, PD-1, TRAC, TRBC, CD3ζ, CTLA-4, LAG-3, CD5, ICOS, OX40, NKG2D, 2B4, CD244, FcεRIγ, BTLA, CD30, GITR, HVEM, DAP10, CD2, NKG2C, LIGHT, DAP12, CD40L (CD154), TIM1, CD226, DR3, CD45, CD80, CD86, CD9, CD16, CD22, CD33, CD37, CD64, SLAM and variants thereof.

In some embodiments, wherein the transmembrane domain comprises a transmembrane domain derived from CD8 or a variant thereof.

In some embodiments, wherein the transmembrane domain comprises an amino acid sequence as set forth in SEQ ID NO: 17 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 17.

In some embodiments, the chimeric antigen receptor further comprises an intracellular signaling domain, wherein the intracellular signaling domain comprises an intracellular signaling domain derived from one or more proteins selected from the group consisting of: CD3ζ, CD3δ, CD3γ, CDR3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

In some embodiments, wherein the intracellular signaling domain comprises a signaling domain derived from CD3ζ.

In some embodiments, wherein the intracellular signaling domain comprises an amino acid sequence as set forth in SEQ ID NO: 19 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 19.

In some embodiments, wherein the chimeric antigen receptor comprises an extracellular antigen-binding domain, a transmembrane domain, and an intracellular signaling domain.

For example, the chimeric antigen receptor comprises an extracellular antigen-binding domain, a transmembrane domain, and an intracellular signaling domain; wherein the extracellular antigen-binding domain may comprise an amino acid sequence as set forth in SEQ ID NO: 23, the transmembrane domain may comprise a transmembrane domain derived from CD8 or a variant thereof, and the intracellular signaling domain may comprise a signaling domain derived from CD3ζ.

For another example, the chimeric antigen receptor comprises an extracellular antigen-binding domain, a transmembrane domain, and an intracellular signaling domain; wherein the extracellular antigen-binding domain may comprise an amino acid sequence as set forth in SEQ ID NO: 23, the transmembrane domain may comprise an amino acid sequence as set forth in SEQ ID NO: 17, and the intracellular signaling domain may comprise an amino acid sequence as set forth in SEQ ID NO: 19.

In some embodiments, wherein the chimeric antigen receptor further comprises an intracellular costimulatory signaling domain, wherein the intracellular costimulatory signaling domain comprises an intracellular costimulatory signaling domain derived from one or more proteins selected from the group consisting of: CD28, 4-1BB (CD137), CD27, CD2, CD7, CD8A, CD8B, OX40, CD226, DR3, SLAM, CDS, ICAM-1, NKG2D, NKG2C, B7-H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, MyD88 and variants thereof.

In some embodiments, wherein the intracellular costimulatory signaling domain is derived from a costimulatory signaling domain of 4-1BB or a variant thereof.

In some embodiments, wherein the intracellular costimulatory signaling domain comprises an amino acid sequence as set forth in SEQ ID NO: 18 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 18.

In some embodiments, the chimeric antigen receptor comprises, from the N-terminus to the C-terminus, an extracellular antigen-binding domain, a transmembrane domain, an intracellular costimulatory signaling domain, and an intracellular signaling domain sequentially.

For example, the chimeric antigen receptor may comprise, from the N-terminus to the C-terminus, an extracellular antigen-binding domain, a transmembrane domain, an intracellular costimulatory signaling domain, and an intracellular signaling domain sequentially; wherein the extracellular antigen-binding domain may comprise an amino acid sequence as set forth in SEQ ID NO: 23, the transmembrane domain may comprise a transmembrane domain derived from CD8 or a variant thereof, the intracellular costimulatory signaling domain may comprise a costimulatory signaling domain derived from 4-1BB or a variant thereof, and the intracellular signaling domain may comprise a signaling domain derived from CD3ζ.

For another example, the chimeric antigen receptor comprises an extracellular antigen binding domain, a transmembrane domain, an intracellular costimulatory signaling domain, and an intracellular signaling domain; wherein the extracellular antigen-binding domain may comprise an amino acid sequence as set forth in SEQ ID NO: 23, the transmembrane domain may comprise an amino acid sequence as set forth in SEQ ID NO: 17, the intracellular costimulatory signaling domain may comprise an amino acid sequence as set forth in SEQ ID NO: 18, and the intracellular signaling domain may comprise an amino acid sequence as set forth in SEQ ID NO: 19.

In some embodiments, wherein the chimeric antigen receptor further comprises a spacer between the transmembrane domain and the extracellular antigen-binding domain, wherein the spacer comprises a hinge region derived from one or more proteins selected from the group consisting of: CD28, CD8, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, LIGHT and variants thereof.

In some embodiments, the spacer comprises a hinge region derived from CD8 or a variant thereof.

In some embodiments, the spacer comprises an amino acid sequence as set forth in SEQ ID NO: 16 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 16.

In some embodiments, the chimeric antigen receptor comprises, from the N-terminus to the C-terminus, an extracellular antigen-binding domain, a spacer, a transmembrane domain, an intracellular costimulatory signaling domain, and an intracellular signaling domain sequentially.

For example, the chimeric antigen receptor comprises, from the N-terminus to the C-terminus, an extracellular antigen-binding domain, a spacer, a transmembrane domain, an intracellular costimulatory signaling domain, and an intracellular signaling domain; wherein the extracellular antigen-binding domain may comprise an amino acid sequence as set forth in SEQ ID NO: 23, the spacer may comprise a hinge region derived from CD8 or a variant thereof, the transmembrane domain may comprise a transmembrane domain derived from CD8 or a variant thereof, the intracellular costimulatory signaling domain may comprise a costimulatory signaling domain derived from 4-1BB or a variant thereof, and the intracellular signaling domain may comprise a signaling domain derived from CD3ζFor another example, the chimeric antigen receptor comprises an extracellular antigen-binding domain, a spacer, a transmembrane domain, an intracellular costimulatory signaling domain, and an intracellular signaling domain; wherein the extracellular antigen-binding domain may comprise an amino acid sequence as set forth in SEQ ID NO: 23, the spacer comprises an amino acid sequence as set forth in SEQ ID NO: 16, the transmembrane domain may comprise an amino acid sequence as set forth in SEQ ID NO: 17, the intracellular costimulatory signaling domain may comprise an amino acid sequence as set forth in SEQ ID NO: 18, and the intracellular signaling domain may comprise an amino acid sequence as set forth in SEQ ID NO: 19.

In some embodiments, the spacer, the transmembrane domain, the intracellular costimulatory signaling domain, and the intracellular signaling domain of the chimeric antigen receptor from the N-terminus to the C-terminus comprise an amino acid sequence as set forth in SEQ ID NO: 24 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 24.

In some embodiments, the chimeric antigen receptor further comprises a signal peptide fragment, wherein the C-terminus of the signal peptide fragment is linked to the N-terminus of the extracellular antigen-binding domain.

In some embodiments, the signal peptide fragment includes a CD8 signal peptide fragment.

In some embodiments, the signal peptide fragment comprises an amino acid sequence as set forth in SEQ ID NO: 20 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 20.

For example, the chimeric antigen receptor comprises, from the N-terminus to the C-terminus, a signal peptide fragment, an extracellular antigen-binding domain, a spacer, a transmembrane domain, an intracellular costimulatory signaling domain, and an intracellular signaling domain sequentially; wherein the signal peptide fragment may comprise a CD8 signal peptide fragment, the extracellular antigen-binding domain may comprise an amino acid sequence as set forth in SEQ ID NO: 23, the spacer may comprise a hinge region derived from CD8 or a variant thereof, the transmembrane domain may comprise a transmembrane domain derived from CD8 or a variant thereof, the intracellular costimulatory signaling domain may comprise a costimulatory signaling domain derived from 4-1BB or a variant thereof, and the intracellular signaling domain may comprise a signaling domain derived from CD3ζ. For another example, the chimeric antigen receptor comprises a signal peptide fragment, an extracellular antigen-binding domain, a spacer, a transmembrane domain, an intracellular costimulatory signaling domain, and an intracellular signaling domain; wherein the signal peptide fragment may comprise an amino acid sequence as set forth in SEQ ID NO: 20, the extracellular antigen-binding domain may comprise an amino acid sequence as set forth in SEQ ID NO: 23, the spacer comprises an amino acid sequence as set forth in SEQ ID NO: 16, the transmembrane domain may comprise an amino acid sequence as set forth in SEQ ID NO: 17, the intracellular costimulatory signaling domain may comprise an amino acid sequence as set forth in SEQ ID NO: 18, and the intracellular signaling domain may comprise an amino acid sequence as set forth in SEQ ID NO: 19.

In some embodiments, the chimeric antigen receptor comprises an amino acid sequence as set forth in SEQ ID NO: 25 or an amino acid sequence having at least about 90%, about 91%, about 92%, about 93%, about 94%, about 95%, about 96%, about 97%, about 98%, about 99% or about 99.5% identity to the amino acid sequence as set forth in SEQ ID NO: 25.

In another aspect, the present application provides an isolated nucleic acid molecule comprising a nucleotide sequence encoding the antigen-binding protein described herein or encoding the chimeric antigen receptor described herein.

The nucleic acid molecules described herein may be isolated. For example, it may be produced or synthesized by: (i) amplification in vitro, e.g., by polymerase chain reaction (PCR), (ii) recombination and cloning, (iii) purification, e.g., separation by enzymatic digestion and gel electrophoresis, or (iv) synthesis, e.g., by chemical synthesis. In some embodiments, the isolated nucleic acid is a nucleic acid molecule prepared by recombinant DNA technology.

In the present application, the nucleic acid encoding the antibody or the antigen-binding fragment thereof can be prepared by a variety of methods known in the art, including but not limited to, overlap extension PCR using restriction fragment manipulation or using synthetic oligonucleotides, as described in Sambrook et al., Molecular Cloning, A Laboratory Manual, Cold Spring Harbor Laboratory Press, Cold Spring Harbor, N.Y., 1989; and Ausube et al., Current Protocols in Molecular Biology, Greene Publishing and Wiley-Interscience, New York N.Y., 1993.

In another aspect, the present application provides a construct comprising the nucleic acid molecule described herein.

In some embodiments, wherein the construct is an expression vector.

In some embodiments, wherein the construct is selected from the group consisting of a DNA vector, an RNA vector, a plasmid, a lentiviral vector, an adenoviral vector, an adeno-associated viral vector, and a retroviral vector.

In another aspect, the present application provides a cell comprising the nucleic acid molecule described herein or the construct described herein, and/or expressing the chimeric antigen receptor described herein. For example, the vector described herein can be introduced into the cell, e.g., a eukaryotic cell, such as a plant-derived cell, fungus or yeast cell. The vector described herein can be introduced into the cell by methods known in the art, such as electroporation, lipofectine transfection, lipofectamine transfection, and the like.

In some embodiments, the cell includes an immune effector cell.

In some embodiments, the cell includes a mammalian cell, such as a human cell.

In some embodiments, the immune effector cell includes a human cell.

In some embodiments, the immune effector cell includes a T cell, a B cell, a natural killer cell (NK cell), a macrophage, an NKT cell, a monocyte, a dendritic cell, a granulocyte, a lymphocyte, a leukocyte, and/or a peripheral blood mononuclear cell. For example, the immune effector cell may be a T cell, such as a human T cell.

In some embodiments, the immune effector cell includes an autologous or non-autologous immune effector cell. For example, the immune effector cell may be a non-autologous human T cell.

In some embodiments, the immune effector cell includes a modified immune effector cell. For example, the modification may comprise down-regulation of expression and/or activity of one or more of the immune rejection-related genes.

For example, the method for preparing an immune effector cell may comprise: introducing the nucleic acid molecule or the vector into an immune effector cell.

In another aspect, the present application provides a method for preparing the isolated antigen-binding protein described herein, which comprises culturing the cell described herein under conditions such that the isolated antigen-binding protein described herein is expressed.

In another aspect, the present application provides a pharmaceutical composition comprising the isolated antigen-binding protein described herein, the immunoconjugate described herein, the chimeric antigen receptor described herein, the nucleic acid molecule described herein, the construct described herein or the cell described herein, and optionally a pharmaceutically acceptable carrier. Such vectors may include (but are not limited to): saline, buffer, glucose, water, glycerol, ethanol, and combinations thereof. The pharmaceutical formulation shall match the route of administration. The pharmaceutical composition described herein may be prepared in the form of injections, for example, using normal saline or an aqueous solution containing glucose and other adjuvants, by a conventional method. The pharmaceutical composition in the form of an injection or a solution is preferably manufactured under sterile conditions. The amount of the active ingredient administered is a therapeutically effective amount. In addition, the antigen-binding protein described herein can also be used with an additional therapeutic agent.

The antigen-binding protein or the pharmaceutical composition described herein can be formulated, administered and applied in a manner consistent with Good Medical Practice. Considerations in this context include the particular disorder being treated, the particular mammal being treated, the clinical condition of the individual patient, the etiology of the disorder, the site of agent delivery, the method of administration, and other factors known to medical practitioners. The therapeutic agent (e.g., anti-HER2 antibody or anti-HER2 CAR-T cell) does not need to be, but are optionally, formulated and/or administered concurrently with one or more agents currently used to prevent or treat the disorder in question. The effective amount of such additional agents depends on the amount of therapeutic agent present in the formulation, the type of disorder or treatment, and other factors discussed above. Those agents can generally be used at any dosage and by any route empirically/clinically determined to be appropriate. The dose of the therapeutic agent administered in the combination therapy can be reduced as compared to the individual therapy. The progress of this therapy is readily monitored by conventional techniques.

In another aspect, the present application provides use of the isolated antigen-binding protein described herein, the immunoconjugate described herein, the chimeric antigen receptor described herein, the nucleic acid molecule described herein, the construct described herein, the cell described herein, or the pharmaceutical composition described herein in preparing a medicament for the prevention and/or treatment of a tumor.

In some embodiments, wherein the tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In some embodiments, wherein the tumor includes an HER2 positive tumor.

In another aspect, the present application provides use of the isolated antigen-binding protein described herein, the immunoconjugate described herein, the chimeric antigen receptor described herein, the nucleic acid molecule described herein, the construct described herein, the cell described herein, or the pharmaceutical composition described herein in preparing a medicament for the prevention and/or treatment of a disease related to abnormal HER2 expression.

In some embodiments, wherein the disease related to abnormal HER2 expression includes a tumor.

In some embodiments, wherein the disease related to abnormal HER2 expression includes an HER2 positive tumor.

In some embodiments, wherein the HER2 positive tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In another aspect, the present application provides a method for preventing and/or treating a tumor, which comprises administering to a subject in need thereof an effective amount of the isolated antigen-binding protein described herein, the immunoconjugate described herein, the chimeric antigen receptor described herein, the nucleic acid molecule described herein, the construct described herein, the cell described herein, or the pharmaceutical composition described herein.

In another aspect, the present application provides a method for preventing and/or treating a disease related to abnormal HER2 expression, which comprises administering to a subject in need thereof an effective amount of the isolated antigen-binding protein described herein, the immunoconjugate described herein, the chimeric antigen receptor described herein, the nucleic acid molecule described herein, the construct described herein, the cell described herein, or the pharmaceutical composition described herein.

In some embodiments, wherein the disease related to abnormal HER2 expression includes a tumor.

In some embodiments, wherein the disease related to abnormal HER2 expression includes an HER2 positive tumor.

In some embodiments, wherein the HER2 positive tumor includes breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

In another aspect, the present application provides a method for detecting HER2 in a biological sample, which comprises making the sample in contact with the antigen-binding protein described herein and detecting a complex, wherein the detecting the complex is indicative of HER2 expression in the sample.

Provided is a method for non-diagnostic detection of an HER2 protein in a sample in vitro, which may comprise the steps of:
(1) making the sample in contact with the isolated antigen-binding protein or immunoconjugate described above in vitro;
(2) detecting the formation of an antigen-antibody complex, wherein the formation of the complex is indicative of the presence of the HER2 protein in the sample. The detection may be qualitative, quantitative or semi-quantitative.

In another aspect, the present application provides a kit comprising the isolated antigen-binding protein described above or the immunoconjugate described above being biotinylated. In some cases, the kit may also comprise a container, instructions for use, buffers, and the like.

Without being limited by any theory, the following examples are intended only to illustrate the antigen-binding protein, preparation method, use and the like of the present application, and are not intended to limit the scope of the present application.

EXAMPLES

Example 1
1.1 Construction of anti-HER2 CAR vector for mRNA Production
The pGEM vector was digested with EcoRI and SalI enzymes and purified by gel purification. The anti-HER2 single chain antibody (scFv) sequence and CAR fragment (from hinge domain to CD3ζ domain) were amplified by PCR, digested with XhoI and EcoRI, and purified by gel purification. The single chain antibody fragment, CAR fragment (from hinge domain to CD3ζ domain) and pGEM vector were ligated with T4 ligase and transformed into competent cells. Correct colonies were selected for further experiments after being confirmed by sanger sequencing. FIG. 1 provides a schematic diagram of a pGEM CAR vector for CAR mRNA generation.

1.2 In Vitro Transcription (IVT) of CAR mRNA The pGEM-CAR plasmid was digested with SpeI enzyme to be enabled linearized. The linearized vector was purified using a PCR purification kit and eluted with RNase-free water. The concentration of DNA was determined using a nanodrop and verified by performing agarose gel electrophoresis for DNA. IVT was performed according to the protocol of the manufacturer (ThermoFisher, Cat No: AM13455). Specifically, 1 µg of template DNA, NTP/ARCA buffer, T7 buffer, GTP, T7 enzyme mix and RNase-free $H_2O$ were added to a 0.2 mL PCR tube in a volume of 20 gL and incubated at 37° C. for 3 h. 3 h later, 2 µL of DNase was added to each reaction and incubated for 15 min at 37 ° C. The tailing procedure was then performed according to the manufacturer's recommendations. IVT mRNA was purified using an RNasy kit (Qiagen). The concentration of RNA was determined using a nanodrop and verified by performing PAGE electrophoresis for DNA.

1.3 Preparation and Characterization of Anti-HER2 CAR-T Cells
A549 tumor cells and T cells were collected and washed 3 times with an Opti-MEM medium. The cell pellet was resuspended in an Opti-MEM medium at a cell concentration of $1 \times 10e^7$/mL. 10 µg, 1 µg, 0.1 µg, 0.01 µg or 0 µg of HER2 protein mRNA was added to 100 ρL of A549 cells and mixed well; 10 µg of anti-HER2 CAR mRNA was added to 100 µL of T cells and mixed well. The parameters on a BTX machine were set: for T cells: 500 V, 0.7 ms; and for A549 tumor cells: 300 V, 0.5 ms. 100 µL of cells mixed with RNA were added to the BTX electroporation cuvette, which was then tapped gently to avoid air bubbles. Electroporation was performed, and then the cells were transferred to a preheated medium and cultured at 37° C.

Figure 2:
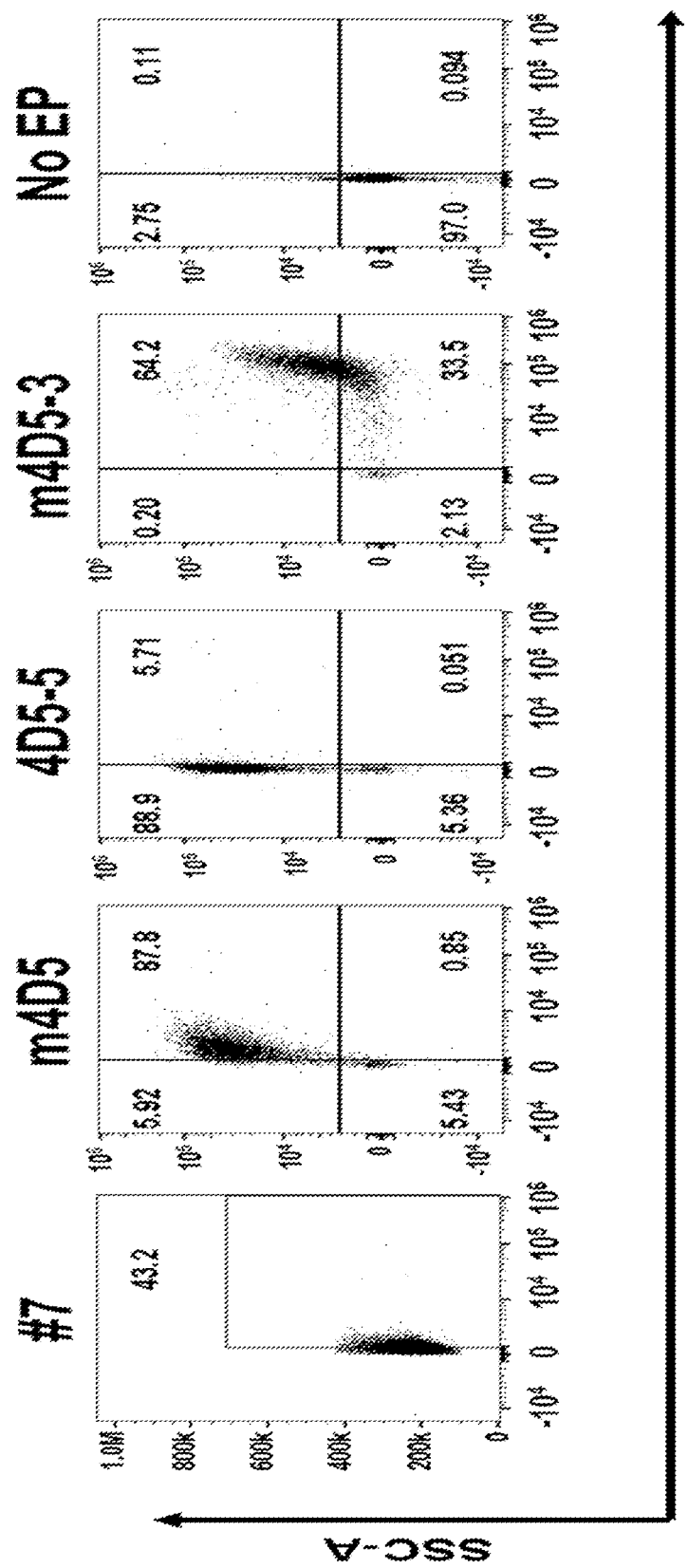
FIG. 2 shows FACS staining results of the binding of anti-HER2 scFv expressed in the CAR-T cells of the present application to HER2-6His protein.
Figure 3:
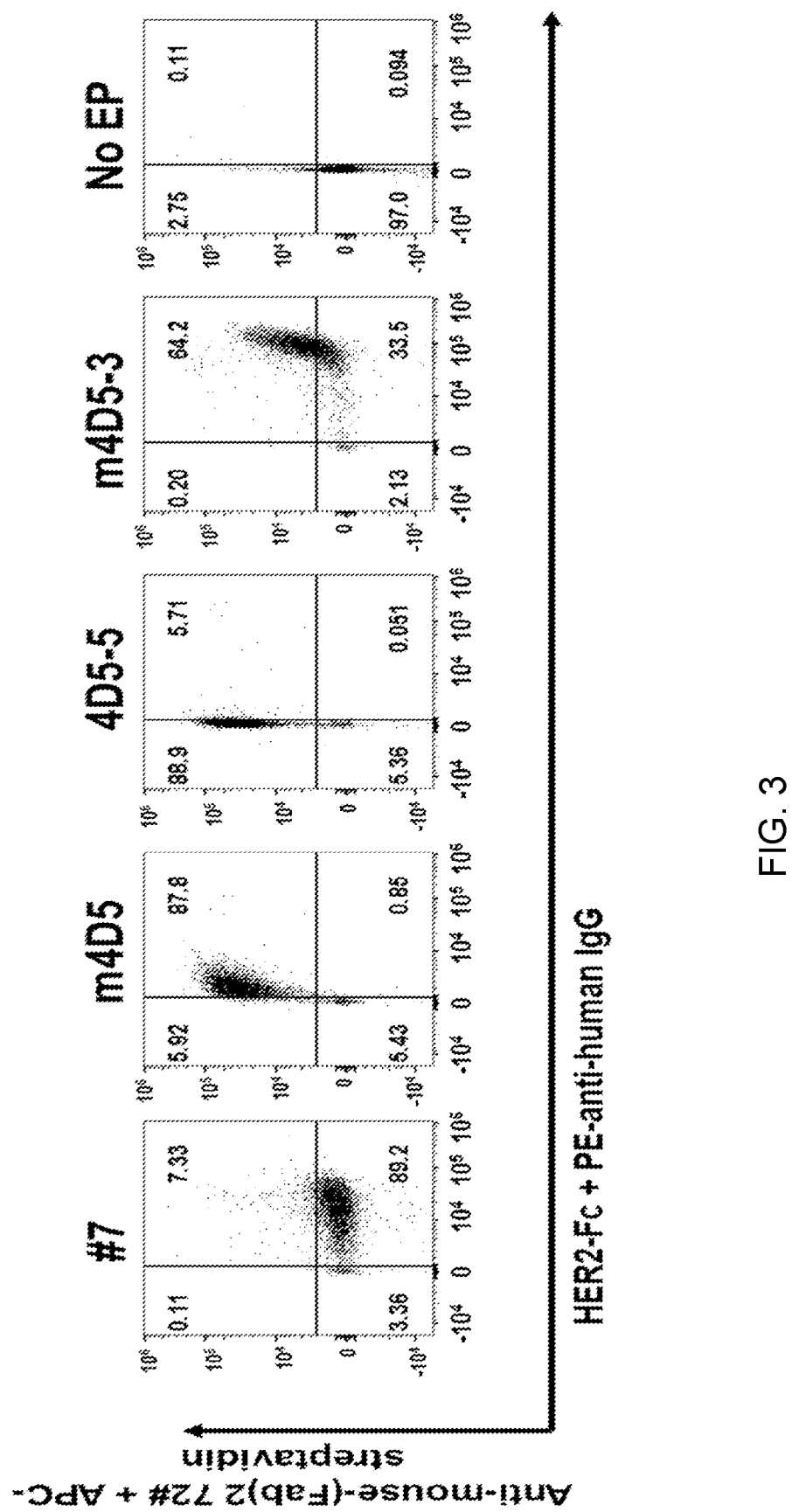
FIG. 3 shows FACS staining results of the binding of anti-HER2 scFv expressed in the CAR-T cells of the present application to HER2-Fc protein and AffiniPure goat anti-mouse IgG-(Fab)$_2$ 072 protein bound by Biotin-SP.
Figure 4A:
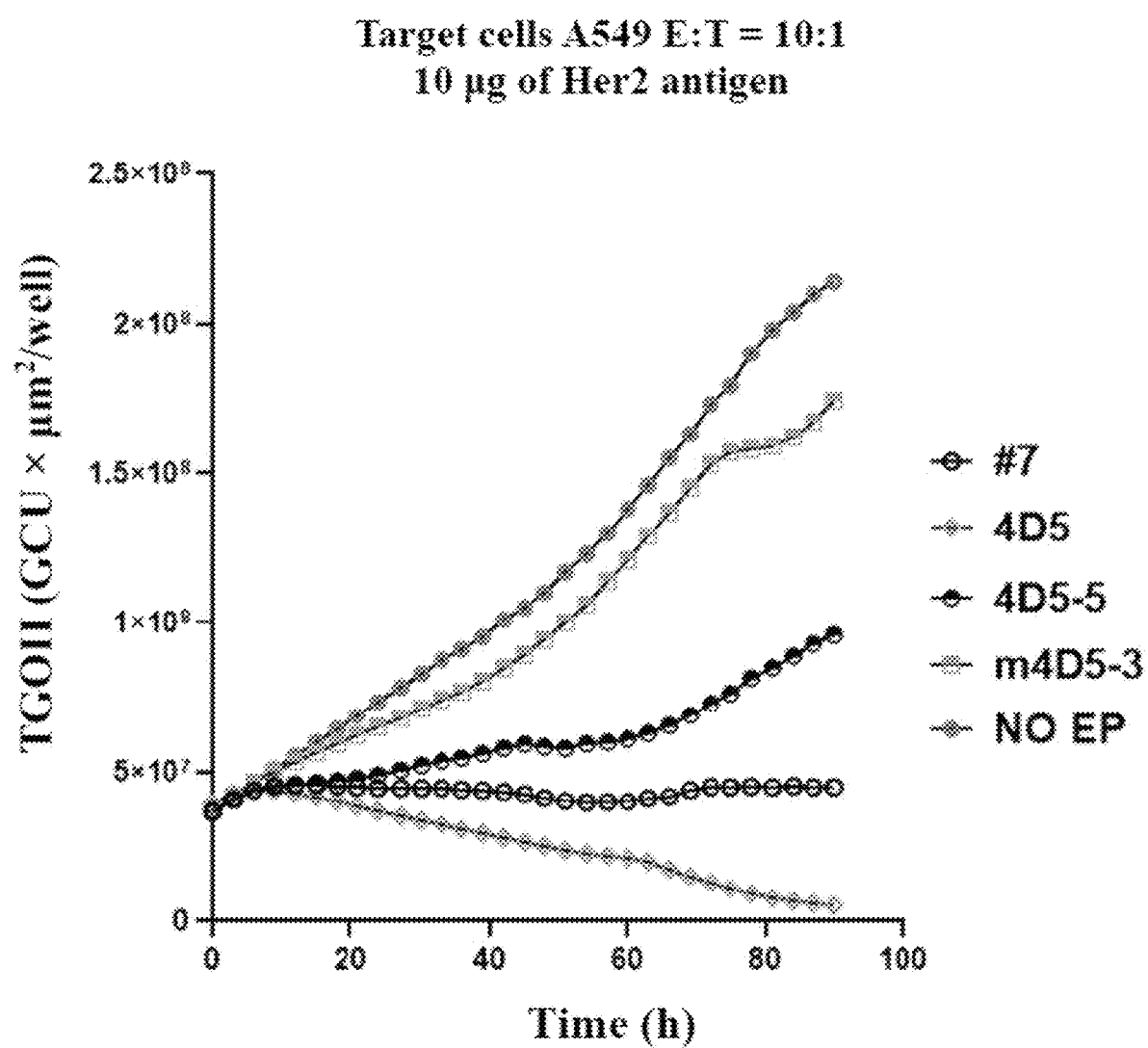
FIGS. 4a-4e show killing curves of the anti-HER2 CAR-T cells described herein for A549-GFP tumor cells electroporated with 10 μg (4a), 1 μg (4b), 0.1 μg (4c), 0.01 μg (4d), and 0 μg (4e) of HER2 mRNAs at an E/T ratio of 10:1.
Figure 4B:
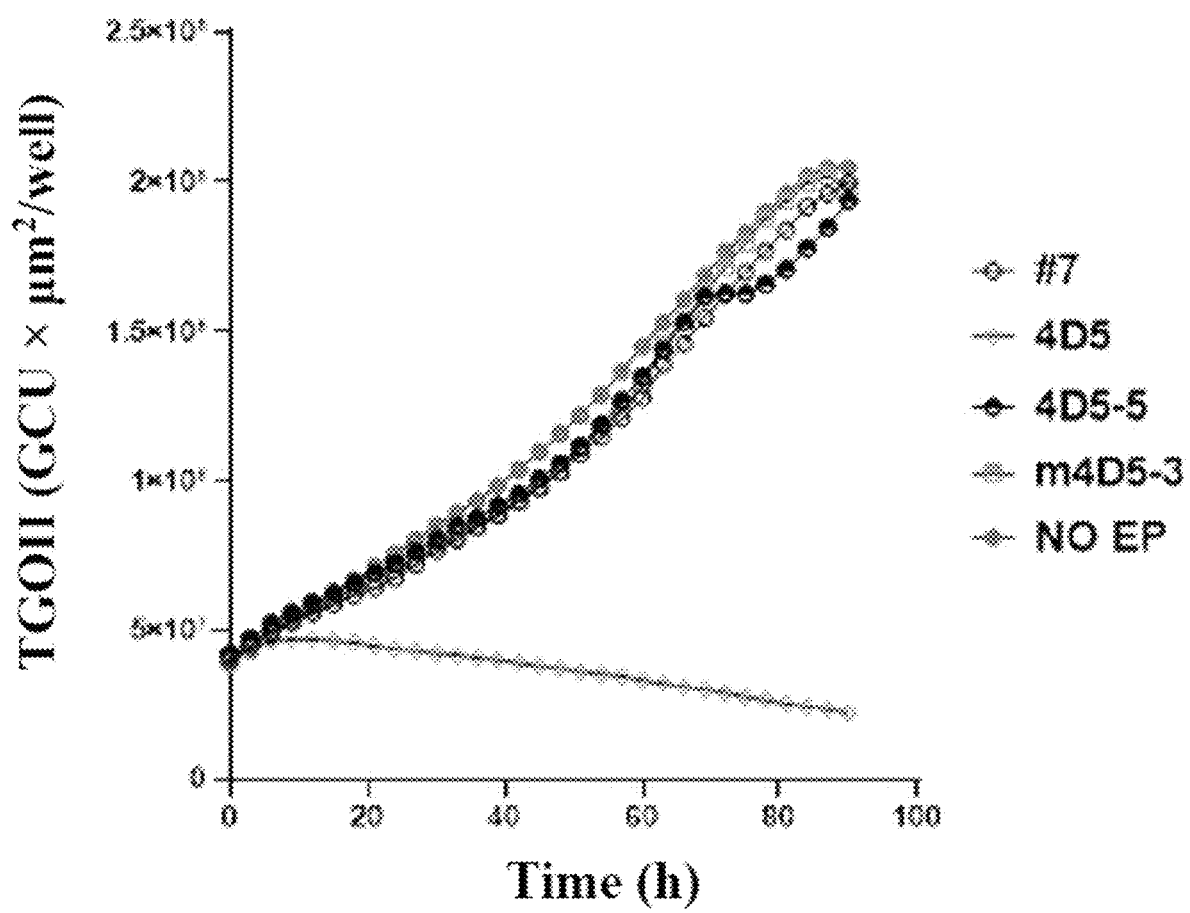
Figure 4C:
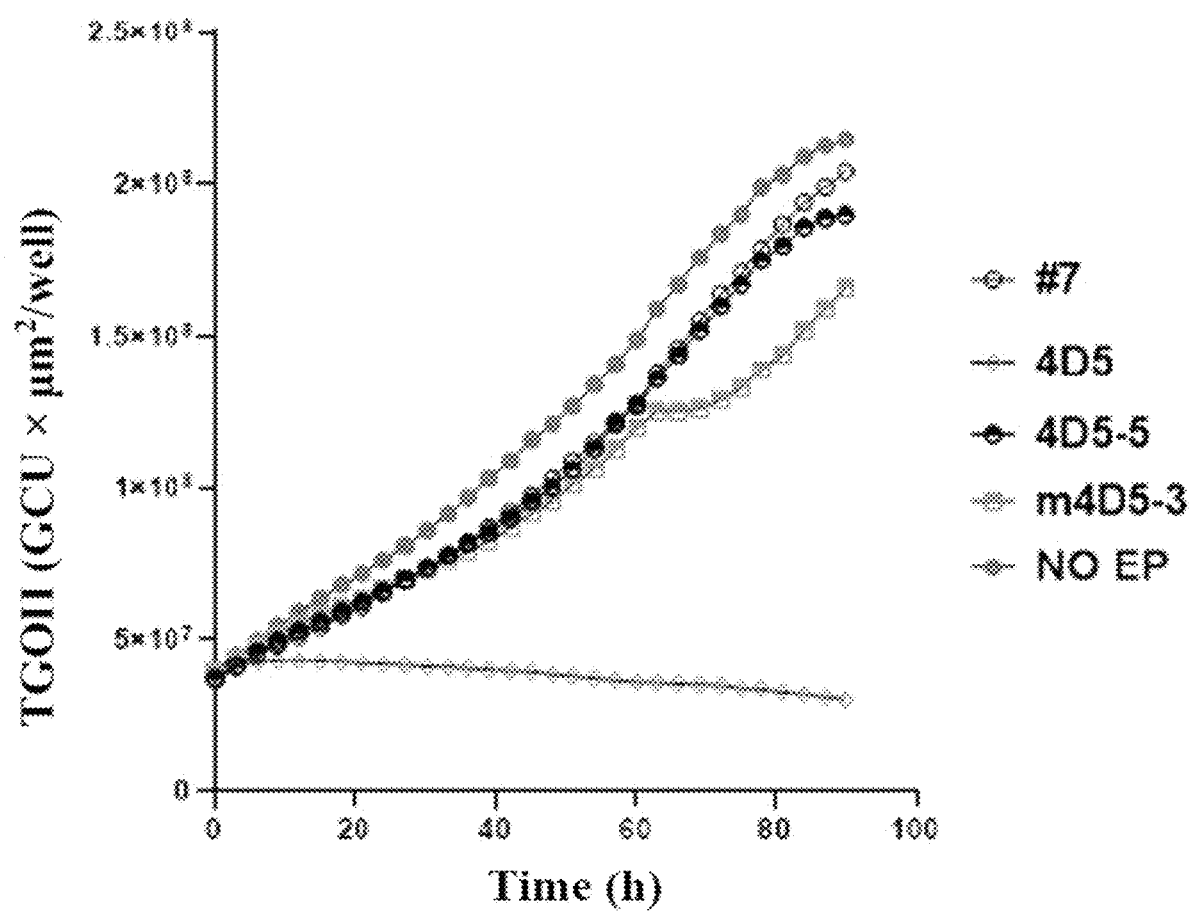
Figure 4D:
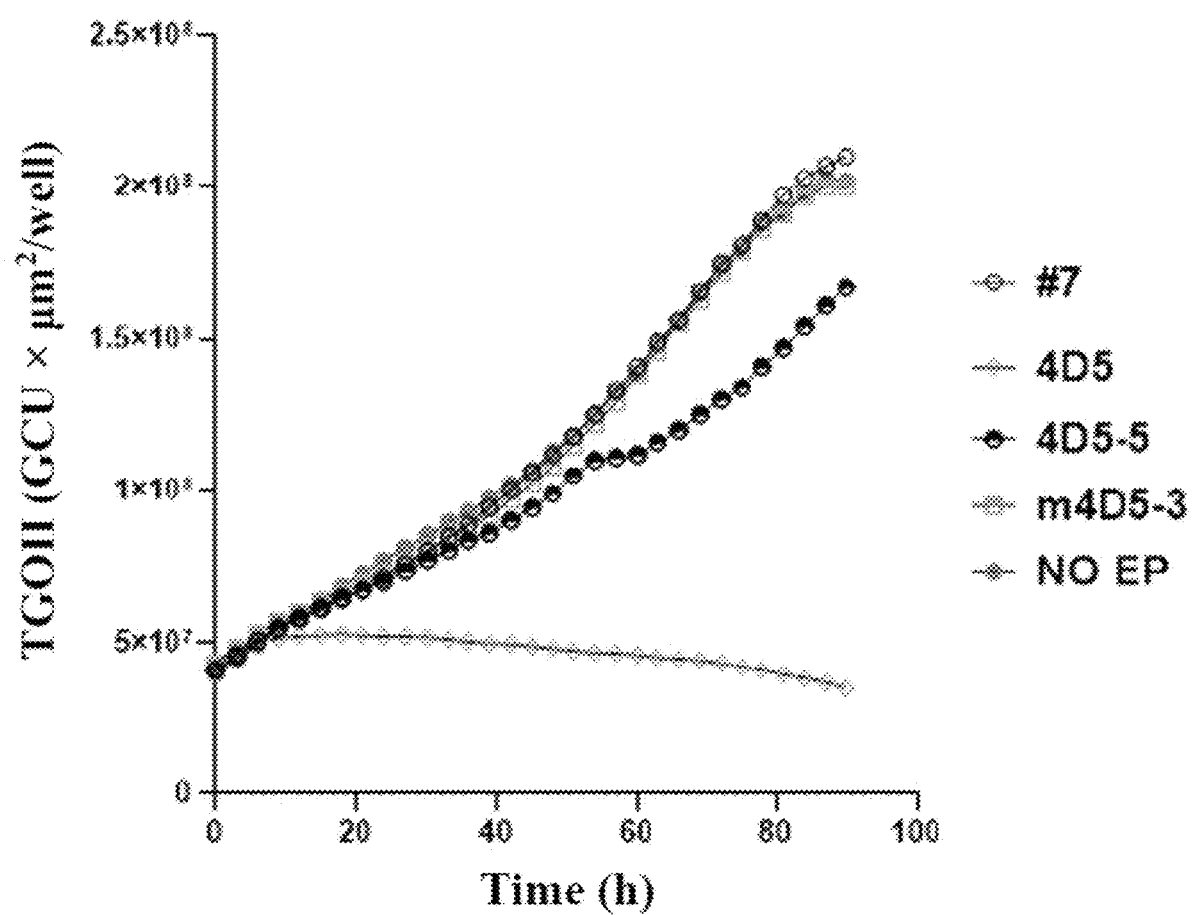
Figure 4E:
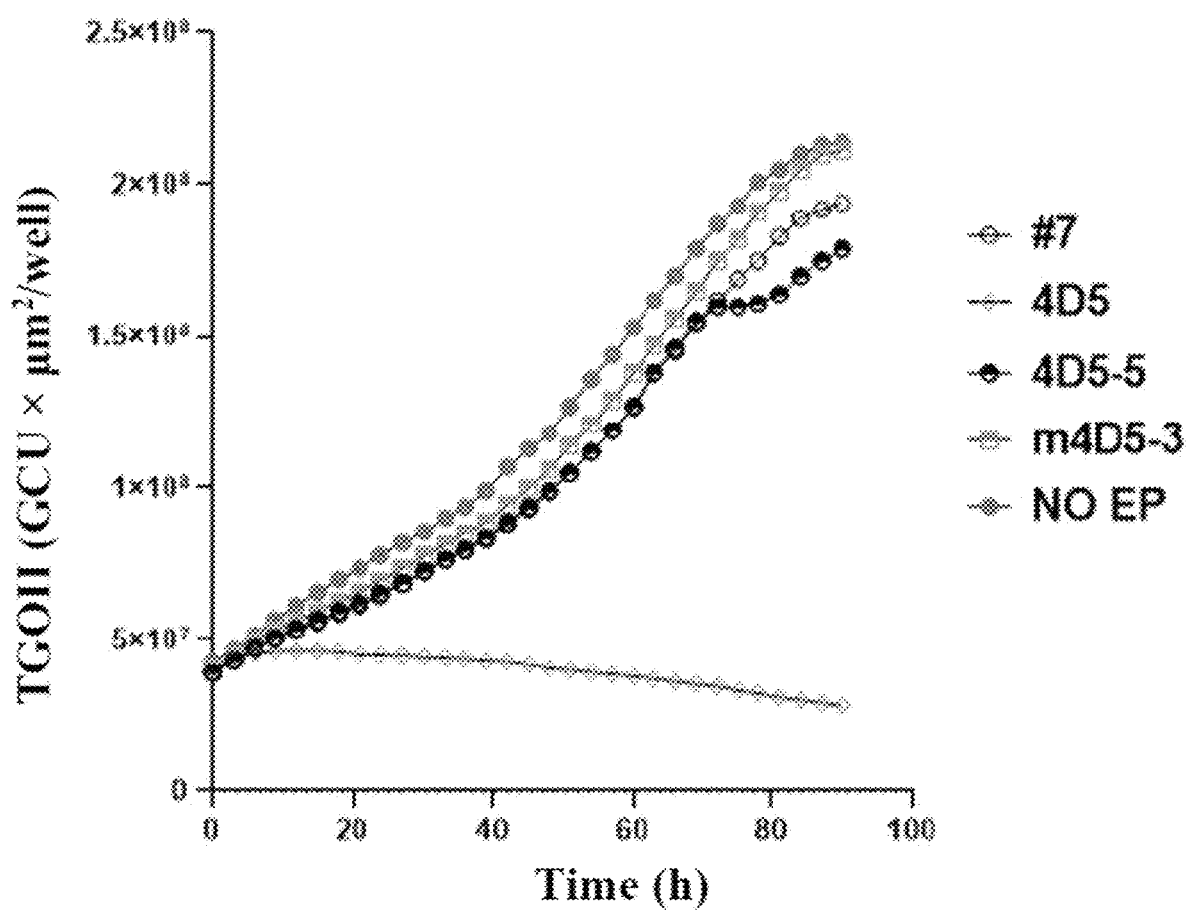
Figure 5A:
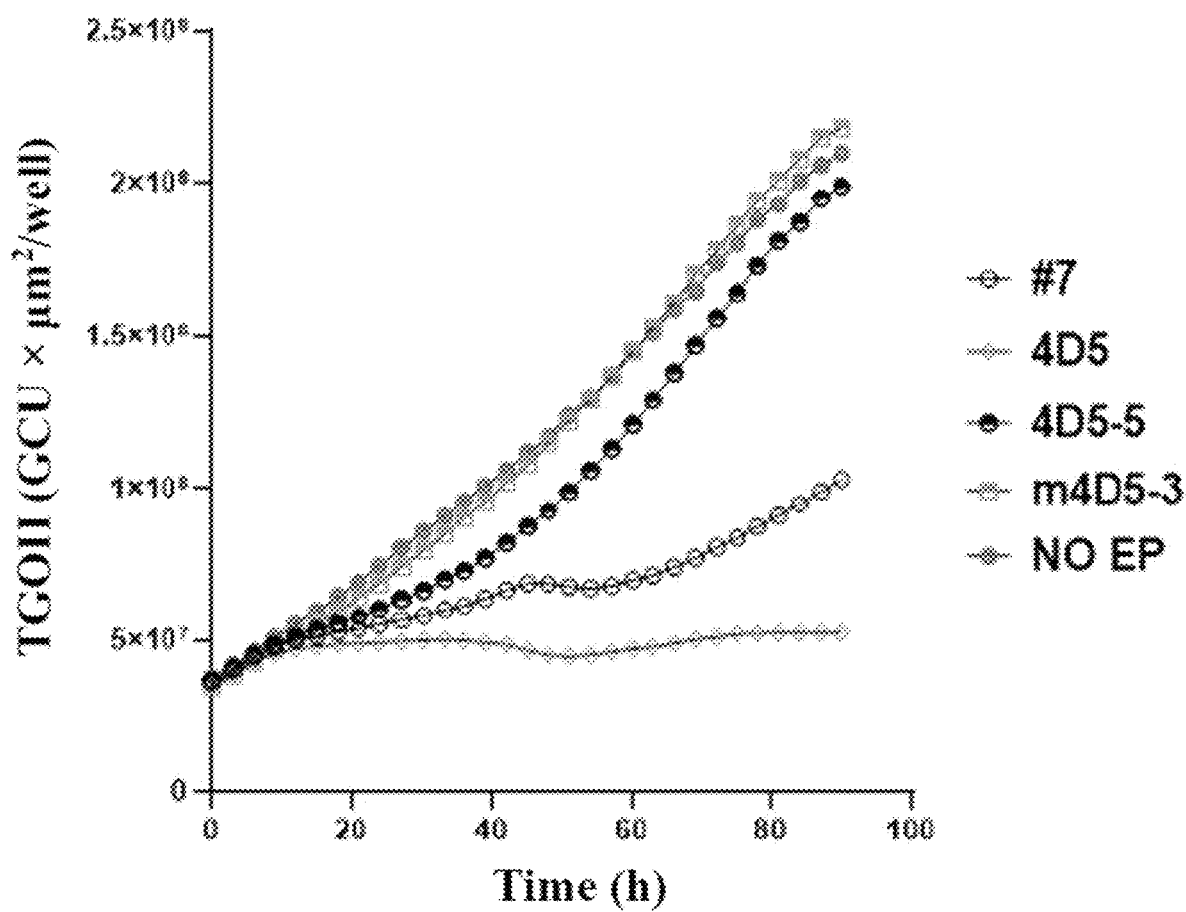
FIGS. 5a-5e show killing curves of the anti-HER2 CAR-T cells described herein for A549-GFP tumor cells electroporated with 10 μ(5a), 1 μg (5b), 0.1 μg (5c), 0.01 μg (5d) and 0 μg (5e) of HER2 mRNAs at an E/T ratio of 1:1.
Figure 5B:
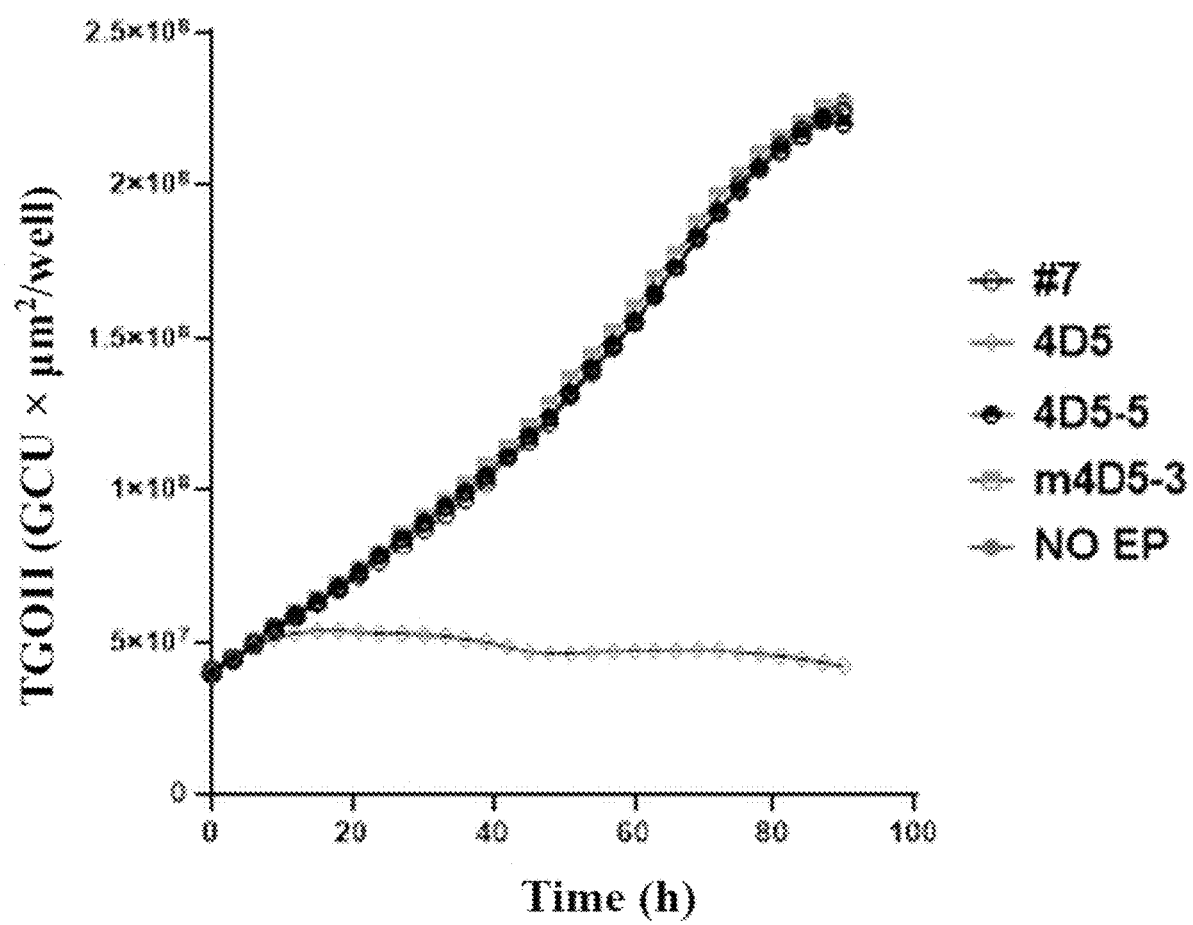
Figure 5C:
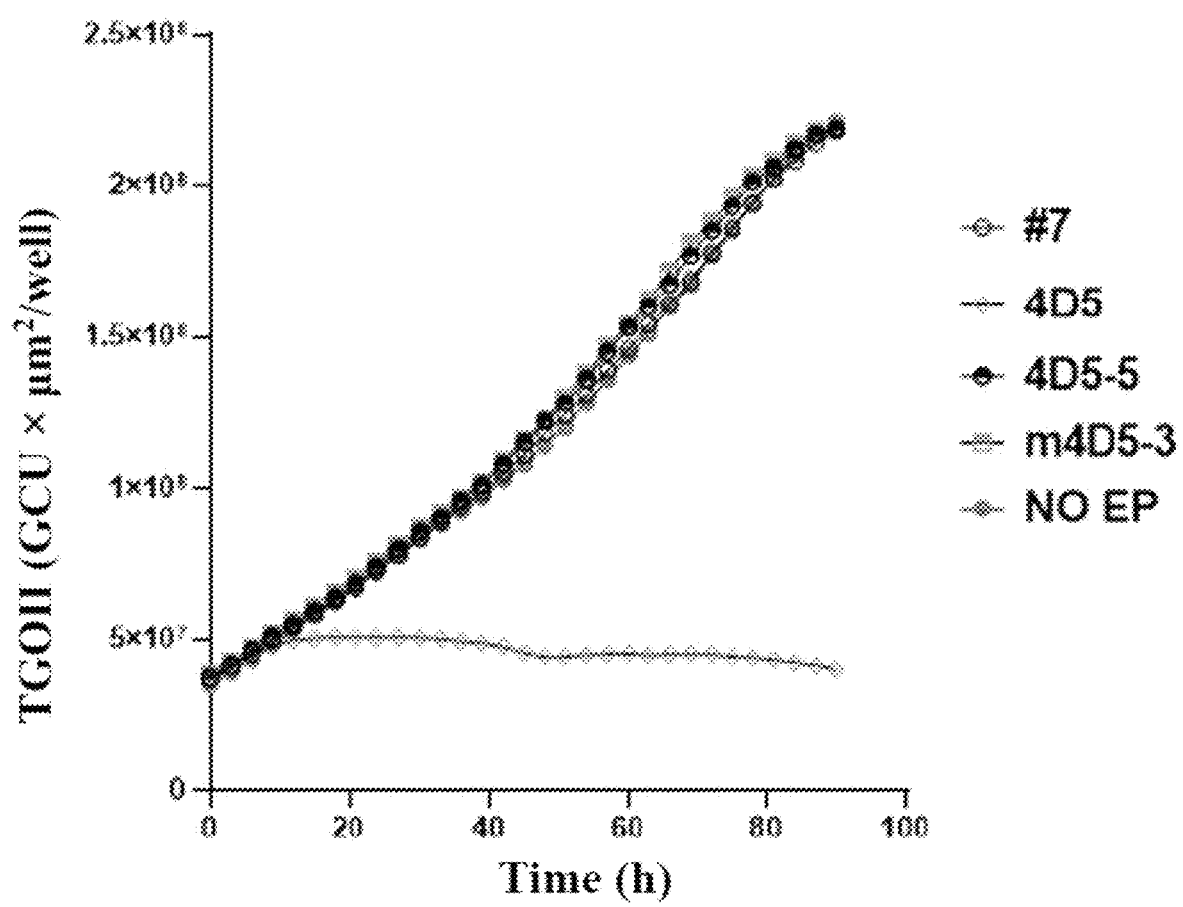
Figure 5D:
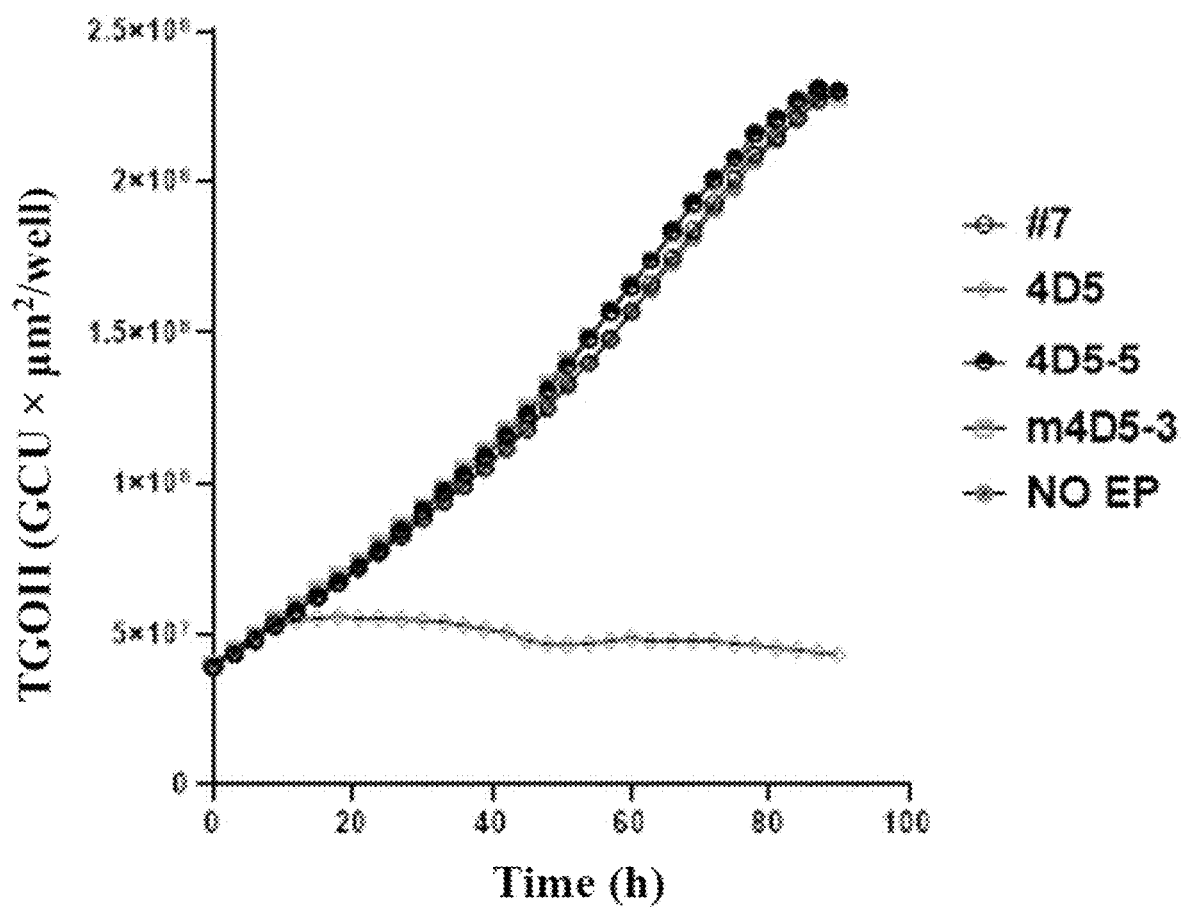
Figure 5E:
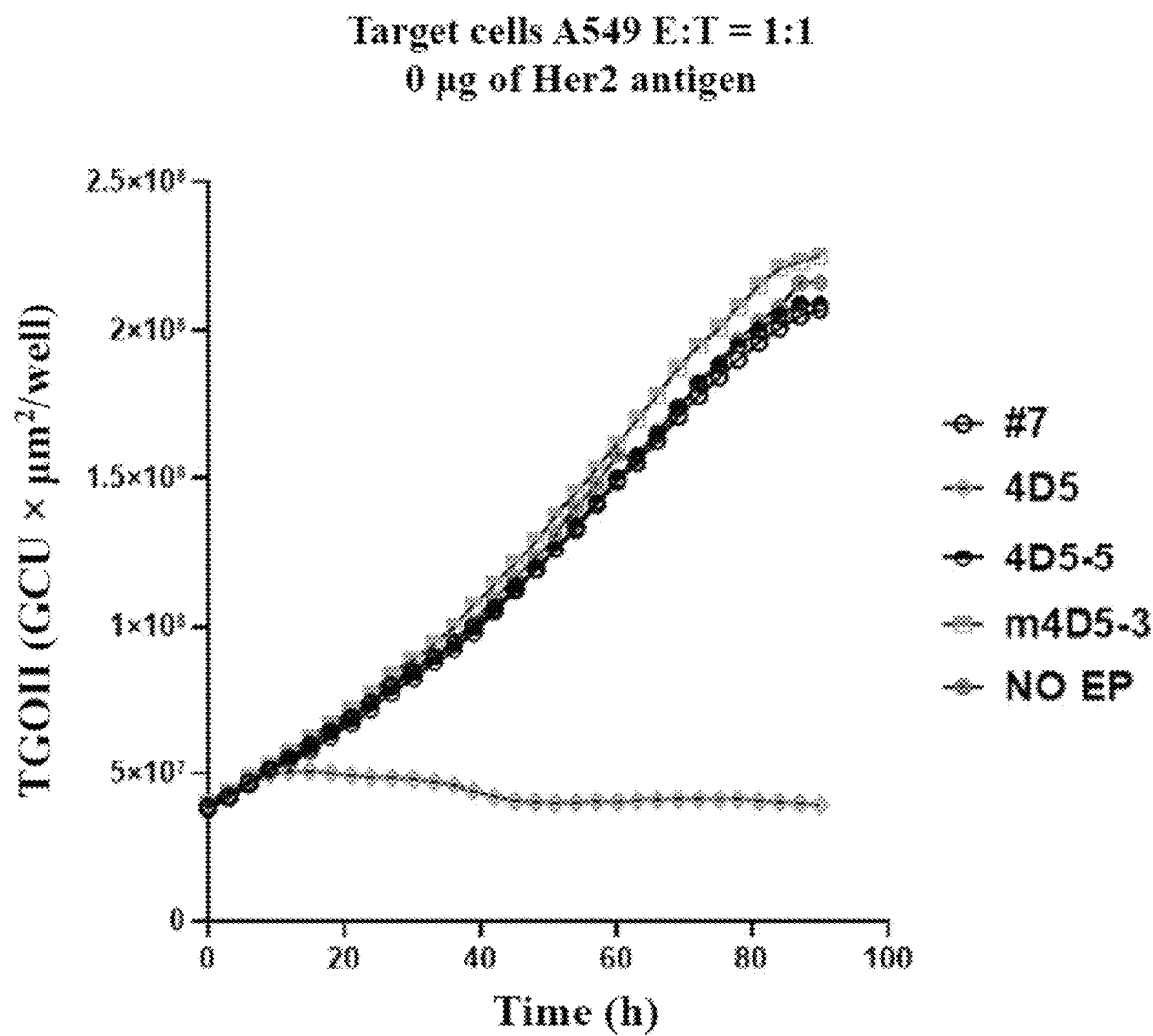

The binding of anti-HER2 CART cells to HER2-Fc recombinant protein, HER2-6His and 072 was determined by FACS staining. As shown in FIG. 2, CAR-T cells (#7) expressing anti-HER2 scFv were able to bind to the HER2-6His protein, and as shown in FIG. 3, CAR-T cells (#7) expressing anti-HER2 scFv were able to bind to the HER2-Fc protein, wherein NO EP was a control T cell without a CAR molecule, m4D5 (SEQ ID NO: 35), 4D5-5 (SEQ ID NO: 33) and m4D5-3 (SEQ ID NO: 34) were control CAR-T cells (Liu etc. Affinity-Tuned ErbB2 or EGFR Chimeric Antigen Receptor T Cells Exhibit an Increased Therapeutic Index against Tumors in Mice. *Cancer Res* 1 Sep. 2015, 75 (17): 3596-3607).

Example 2. In Vitro Cytotoxicity Assay on Anti-HER2 CAR-T Cells

EGFP-A549 cells electroporated with varying amounts of mRNA encoding the HER2 antigen were seeded into a flat bottom 96-well plate at 3000 cells/100 µL/well. CAR-T cells were diluted to appropriate concentrations and seeded at 100 µL/well into tumor cells at different E/T ratios, e.g., 10:1 or 1:1. The co-culture plate was placed into the IncuCyte S3 machine and the scan parameters were set. After scanning for 3 days, the total green object integrated intensity (GCU× µm²/Well) was analyzed to calculate the killing efficiency.

FIGS. 4a-4e show the killing curves of anti-HER2 CAR-T cells against A549-GFP tumor cells electroporated with 10 µg, 1 µg, 0.1 µg, 0.01 µg or 0 µg of mRNAs encoding the HER2 antigen at an E/T ratio of 10:1. FIGS. 4a-4e show that the killing effect of anti-HER2 CAR-T cells (#7) on A549 tumor cells expressing HER2 is intermediate between that on m4D5 and on 4D5-5.

FIGS. 5a-5e show the killing curves of anti-HER2 CAR-T cells against A549-GFP tumor cells electroporated with 10 μg, 1 μg, 0.1 μgg, 0.01 μg or 0 μg of mRNAs encoding the HER2 antigen at an E/T ratio of 1:1. FIGS. 5a-5e show that the killing effect of anti-HER2 CAR-T cells (#7) on A549 tumor cells expressing HER2 is intermediate between that on m4D5 and on 4D5-5.

The invention claimed is:

1. An isolated antigen-binding protein binding HER2 and comprising a VH and a VL, wherein the VH comprises an HCDR1, an HCDR2 and an HCDR3, wherein the HCDR1 comprises an amino acid sequence as set forth in SEQ ID NO: 10, the HCDR2 comprises an amino acid sequence as set forth in SEQ ID NO: 12, and the HCDR3 comprises an amino acid sequence as set forth in SEQ ID NO: 14; and the VL comprises an LCDR1, an LCDR2 and an LCDR3, wherein the LCDR1 comprises an amino acid sequence as set forth in SEQ ID NO: 2, the LCDR2 comprises an amino acid sequence as set forth in SEQ ID NO: 4, and the LCDR3 comprises an amino acid sequence as set forth in SEQ ID NO: 6.

2. The isolated antigen-binding protein of claim 1, comprising a VH and a VL, wherein the VH comprises an amino acid sequence as set forth in SEQ ID NO: 22, and the VL comprises an amino acid sequence as set forth in SEQ ID NO: 21.

3. The isolated antigen-binding protein of claim 1, comprising an antibody or an antigen-binding fragment thereof.

4. The isolated antigen-binding protein of claim 3 wherein the antibody or the antigen-binding fragment thereof comprises a monoclonal antibody, a polyclonal antibody, a chimeric antibody, a humanized antibody, a fully human antibody, a Fab, a Fab', a Fv fragment, a F(ab')$_2$, an scFv, and/or a di-scFv.

5. The isolated antigen-binding protein of claim 1, comprising an scFv, wherein the VH and the VL are linked by a linker.

6. The isolated antigen-binding protein of claim 5, wherein the linker comprises an amino acid sequence as set forth in SEQ ID NO: 8.

7. The isolated antigen-binding protein of claim 1, comprising an amino acid sequence as set forth in SEQ ID NO: 23.

8. A chimeric antigen receptor (CAR) comprising an extracellular antigen-binding domain, a transmembrane domain, and an intracellular signaling domain, wherein the extracellular antigen-binding domain comprises the isolated antigen-binding protein of claim 1.

9. The CAR of claim 8, wherein the transmembrane domain comprises a transmembrane domain derived from one or more proteins selected from the group consisting of: CD8, CD28, CD3ε (CD3e), 4-1BB, CD4, CD27, CD7, PD-1, TRAC, TRBC, CD3ζ, CTLA-4, LAG-3, CDS, ICOS, OX40, NKG2D, 2B4, CD244, FcεRIγ, BTLA, CD30, GITR, HVEM, DAP10, CD2, NKG2C, LIGHT, DAP12, CD40L (CD154), TIM1, CD226, DR3, CD45, CD80, CD80, CD9, CD16, CD22, CD33, CD37, CD64, SLAM and variants thereof.

10. The CAR of claim 8, wherein the transmembrane domain comprises an amino acid sequence as set forth in SEQ ID NO: 17.

11. The CAR of claim 8, wherein the intracellular signaling domain comprises an intracellular signaling domain derived from one or more proteins selected from the group consisting of: CD3ζ; CD3δ, CD3γ, CD3ε, CD79a, CD79b, FcεRIγ, FcεRIβ, FcγRIIa, bovine leukemia virus gp30, Epstein-Barr virus (EBV) LMP2A, simian immunodeficiency virus PBj14 Nef, DAP10, DAP-12, and a domain comprising at least one ITAM.

12. The CAR of claim 8, wherein the intracellular signaling domain comprises an amino acid sequence as set forth in SEQ ID NO: 19.

13. The CAR of claim 8, further comprising an intracellular costimulatory signaling domain, wherein the intracellular costimulatory signaling domain comprises an intracellular costimulatory signaling domain derived from one or more proteins selected from the group consisting of: CD28, 4-1BB (CD137), CD27, CD2, CD7, CD8A, CD8B, OX40, CD226, DR3, SLAM, CDS, ICAM-1, NKG2D, NKG2C, B7-H3, 2B4, FcεRIγ, BTLA, GITR, HVEM, DAP10, DAP12, CD30, CD40, CD40L, TIM1, PD-1, LFA-1, LIGHT, JAML, CD244, CD100, ICOS, CD40, MyD88 and variants thereof.

14. The CAR of claim 13, wherein the intracellular costimulatory signaling domain comprises an amino acid sequence as set forth in SEQ ID NO: 18.

15. The CAR of claim 13, comprising, from the N-terminus to the C-terminus, an extracellular antigen-binding domain, a transmembrane domain, an intracellular costimulatory signaling domain, and an intracellular signaling domain sequentially.

16. The CAR of claim 8, further comprising a spacer between the transmembrane domain and the extracellular antigen-binding domain, wherein the spacer comprises a hinge region derived from one or more proteins selected from the group consisting of: CD28, CD8, IgG1, IgG4, IgD, 4-1BB, CD4, CD27, CD7, CD8A, PD-1, ICOS, OX40, NKG2D, NKG2C, FcεRIγ, BTLA, GITR, DAP10, TIM1, SLAM, CD30, LIGHT and variants thereof.

17. The CAR of claim 16, wherein the spacer comprises an amino acid sequence as set forth in SEQ ID NO: 16.

18. The CAR of claim 16, comprising, from the N-terminus to the C-terminus, an extracellular antigen-binding domain, a spacer, a transmembrane domain, an intracellular costimulatory signaling domain, and an intracellular signaling domain sequentially.

19. The CAR of claim 18, wherein the spacer, the transmembrane domain, the intracellular costimulatory signaling domain, and the intracellular signaling domain of the CAR from the N-terminus to the C-terminus comprise an amino acid sequence as set forth in SEQ ID NO: 24.

20. The CAR of claim 8, further comprising a signal peptide fragment, wherein the C-terminus of the signal peptide fragment is linked to the N-terminus of the extracellular antigen-binding domain.

21. The CAR of claim 20, wherein the signal peptide fragment comprises an amino acid sequence as set forth in SEQ ID NO: 20.

22. The CAR of claim 8, comprising an amino acid sequence as set forth in SEQ ID NO: 25.

23. A cell comprising the nucleic acid molecule encoding the CAR of claim 8.

24. The cell of claim 23, comprising an immune effector cell.

25. The cell of claim 24, wherein the immune effector cell comprises a T cell, a B cell, an NK cell, a macrophage, an NKT cell, a monocyte, a dendritic cell, a granulocyte, a lymphocyte, a leukocyte, and/or a peripheral blood mononuclear cell.

26. The cell of claim 25, wherein the cell comprises a CAR-T cell or a CAR-NK cell.

27. A method of treating a HER2 positive tumor in a subject in need thereof, comprising administering to the subject a therapeutically effective amount of the cell of claim 26.

28. The method of claim 27, wherein the HER2 positive tumor is breast cancer, gastric cancer, ovarian cancer, cervical cancer, urothelial cancer, esophageal cancer, bladder cancer, colorectal cancer, endometrial cancer, kidney cancer, lung cancer, pancreatic cancer, head and neck cancer, sarcoma, glioblastoma, prostate cancer, and/or thyroid cancer.

* * * * *

```
                            SEQUENCE LISTING

Sequence total quantity: 38
SEQ ID NO: 1            moltype = AA   length = 22
FEATURE                 Location/Qualifiers
source                  1..22
                        mol_type = protein
                        organism = synthetic construct
SEQUENCE: 1
QSALTQPASV SGSPGQSITI SC                                                  22

SEQ ID NO: 2            moltype = AA   length = 14
FEATURE                 Location/Qualifiers
source                  1..14
                        mol_type = protein
                        organism = synthetic construct
SEQUENCE: 2
TGTSSDVGGY DYVS                                                           14

SEQ ID NO: 3            moltype = AA   length = 15
FEATURE                 Location/Qualifiers
source                  1..15
                        mol_type = protein
                        organism = synthetic construct
SEQUENCE: 3
WYQQHPGKAP KLMIY                                                          15

SEQ ID NO: 4            moltype = AA   length = 7
FEATURE                 Location/Qualifiers
source                  1..7
                        mol_type = protein
                        organism = synthetic construct
SEQUENCE: 4
DVSNRPS                                                                    7

SEQ ID NO: 5            moltype = AA   length = 32
FEATURE                 Location/Qualifiers
source                  1..32
                        mol_type = protein
                        organism = synthetic construct
SEQUENCE: 5
GVSNRFSGSK SGNTASLTIS GLQAEDEADY YC                                       32

SEQ ID NO: 6            moltype = AA   length = 10
FEATURE                 Location/Qualifiers
source                  1..10
                        mol_type = protein
                        organism = synthetic construct
SEQUENCE: 6
SSYAGSNNVV                                                                10

SEQ ID NO: 7            moltype = AA   length = 10
FEATURE                 Location/Qualifiers
source                  1..10
                        mol_type = protein
                        organism = synthetic construct
SEQUENCE: 7
FGGGTKLTVL                                                                10

SEQ ID NO: 8            moltype = AA   length = 15
FEATURE                 Location/Qualifiers
source                  1..15
                        mol_type = protein
                        organism = synthetic construct
SEQUENCE: 8
GGGGSGGGGS GGGGS                                                          15

SEQ ID NO: 9            moltype = AA   length = 30
FEATURE                 Location/Qualifiers
source                  1..30
                        mol_type = protein
                        organism = synthetic construct
SEQUENCE: 9
```

```
QVQLVQSGAE VKKPGSSVKV SCKASGGTFS                                               30

SEQ ID NO: 10           moltype = AA  length = 5
FEATURE                 Location/Qualifiers
source                  1..5
                        mol_type = protein
                        organism = synthetic construct
SEQUENCE: 10
SYAIS                                                                          5

SEQ ID NO: 11           moltype = AA  length = 14
FEATURE                 Location/Qualifiers
source                  1..14
                        mol_type = protein
                        organism = synthetic construct
SEQUENCE: 11
WVRQAPGQGL EWMG                                                                14

SEQ ID NO: 12           moltype = AA  length = 17
FEATURE                 Location/Qualifiers
source                  1..17
                        mol_type = protein
                        organism = synthetic construct
SEQUENCE: 12
GIIPIFGTAN YAQKFQG                                                             17

SEQ ID NO: 13           moltype = AA  length = 32
FEATURE                 Location/Qualifiers
source                  1..32
                        mol_type = protein
                        organism = synthetic construct
SEQUENCE: 13
RVTITADEST STAYMELSSL RSEDTAVYYC AR                                            32

SEQ ID NO: 14           moltype = AA  length = 13
FEATURE                 Location/Qualifiers
source                  1..13
                        mol_type = protein
                        organism = synthetic construct
SEQUENCE: 14
GGVGAVRGHA FDI                                                                 13

SEQ ID NO: 15           moltype = AA  length = 11
FEATURE                 Location/Qualifiers
source                  1..11
                        mol_type = protein
                        organism = synthetic construct
SEQUENCE: 15
WGQGTMVTVS S                                                                   11

SEQ ID NO: 16           moltype = AA  length = 45
FEATURE                 Location/Qualifiers
source                  1..45
                        mol_type = protein
                        organism = synthetic construct
SEQUENCE: 16
TTTPAPRPPT PAPTIASQPL SLRPEACRPA AGGAVHTRGL DFACD                              45

SEQ ID NO: 17           moltype = AA  length = 24
FEATURE                 Location/Qualifiers
source                  1..24
                        mol_type = protein
                        organism = synthetic construct
SEQUENCE: 17
IYIWAPLAGT CGVLLLSLVI TLYC                                                     24

SEQ ID NO: 18           moltype = AA  length = 42
FEATURE                 Location/Qualifiers
source                  1..42
                        mol_type = protein
                        organism = synthetic construct
SEQUENCE: 18
KRGRKKLLYI FKQPFMRPVQ TTQEEDGCSC RFPEEEEGGC EL                                 42

SEQ ID NO: 19           moltype = AA  length = 112
FEATURE                 Location/Qualifiers
source                  1..112
                        mol_type = protein
                        organism = synthetic construct
```

```
SEQUENCE: 19
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 20            moltype = AA  length = 21
FEATURE                  Location/Qualifiers
source                   1..21
                         mol_type = protein
                         organism = synthetic construct
SEQUENCE: 20
MALPVTALLL PLALLLHAAR P                                              21

SEQ ID NO: 21            moltype = AA  length = 110
FEATURE                  Location/Qualifiers
source                   1..110
                         mol_type = protein
                         organism = synthetic construct
SEQUENCE: 21
QSALTQPASV SGSPGQSITI SCTGTSSDVG GYDYVSWYQQ HPGKAPKLMI YDVSNRPSGV    60
SNRFSGSKSG NTASLTISGL QAEDEADYYC SSYAGSNNVV FGGGTKLTVL               110

SEQ ID NO: 22            moltype = AA  length = 122
FEATURE                  Location/Qualifiers
source                   1..122
                         mol_type = protein
                         organism = synthetic construct
SEQUENCE: 22
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCARGG VGAVRGHAFD IWGQGTMVTV    120
SS                                                                   122

SEQ ID NO: 23            moltype = AA  length = 247
FEATURE                  Location/Qualifiers
source                   1..247
                         mol_type = protein
                         organism = synthetic construct
SEQUENCE: 23
QSALTQPASV SGSPGQSITI SCTGTSSDVG GYDYVSWYQQ HPGKAPKLMI YDVSNRPSGV    60
SNRFSGSKSG NTASLTISGL QAEDEADYYC SSYAGSNNVV FGGGTKLTVL GGGGSGGGGS    120
GGGGSQVQLV QSGAEVKKPG SSVKVSCKAS GGTFSSYAIS WVRQAPGQGL EWMGGIIPIF    180
GTANYAQKFQ GRVTITADES TSTAYMELSS LRSEDTAVYY CARGGVGAVR GHAFDIWGQG    240
TMVTVSS                                                              247

SEQ ID NO: 24            moltype = AA  length = 223
FEATURE                  Location/Qualifiers
source                   1..223
                         mol_type = protein
                         organism = synthetic construct
SEQUENCE: 24
TTTPAPRPPT PAPTIASQPL SLRPEACRPA AGGAVHTRGL DFACDIYIWA PLAGTCGVLL    60
LSLVITLYCK RGRKLLYIF KQPFMRPVQT TQEEDGCSCR FPEEEEGGCE LRVKFSRSAD    120
APAYKQGQNQ LYNELNLGRR EEYDVLDKRR GRDPEMGGKP RRKNPQEGLY NELQKDKMAE    180
AYSEIGMKGE RRRGKGHDGL YQGLSTATKD TYDALHMQAL PPR                      223

SEQ ID NO: 25            moltype = AA  length = 470
FEATURE                  Location/Qualifiers
source                   1..470
                         mol_type = protein
                         organism = synthetic construct
SEQUENCE: 25
QSALTQPASV SGSPGQSITI SCTGTSSDVG GYDYVSWYQQ HPGKAPKLMI YDVSNRPSGV    60
SNRFSGSKSG NTASLTISGL QAEDEADYYC SSYAGSNNVV FGGGTKLTVL GGGGSGGGGS    120
GGGGSQVQLV QSGAEVKKPG SSVKVSCKAS GGTFSSYAIS WVRQAPGQGL EWMGGIIPIF    180
GTANYAQKFQ GRVTITADES TSTAYMELSS LRSEDTAVYY CARGGVGAVR GHAFDIWGQG    240
TMVTVSSTTT PAPRPPTPAP TIASQPLSLR PEACRPAAGG AVHTRGLDFA CDIYIWAPLA    300
GTCGVLLLSL VITLYCKRGR KKLLYIFKQP FMRPVQTTQE EDGCSCRFPE EEEGGCELRV    360
KFSRSADAPA YKQGQNQLYN ELNLGRREEY DVLDKRRGRD PEMGGKPRRK NPQEGLYNEL    420
QKDKMAEAYS EIGMKGERRR GKGHDGLYQG LSTATKDTYD ALHMQALPPR               470

SEQ ID NO: 26            moltype = DNA  length = 63
FEATURE                  Location/Qualifiers
source                   1..63
                         mol_type = other DNA
                         organism = synthetic construct
SEQUENCE: 26
atggcttac cagtgaccgc cttgctcctg ccgctggcct tgctgctcca cgccgccagg     60
ccg                                                                  63

SEQ ID NO: 27            moltype = DNA  length = 135
```

| FEATURE | Location/Qualifiers |
|---|---|
| source | 1..135<br>mol_type = other DNA<br>organism = synthetic construct |

SEQUENCE: 27
```
accacgacgc cagcgccgcg accaccaaca ccggcgccca ccatcgcgtc gcagccctg    60
tccctgcgcc cagaggcgtg ccggccagcg gcggggggcg cagtgcacac gaggggggctg  120
gacttcgcct gtgat                                                    135
```

| SEQ ID NO: 28 | moltype = DNA  length = 72 |
|---|---|
| FEATURE | Location/Qualifiers |
| source | 1..72<br>mol_type = other DNA<br>organism = synthetic construct |

SEQUENCE: 28
```
atctacatct gggcgccctt ggccgggact tgtggggtcc ttctcctgtc actggttatc    60
accctttact gc                                                       72
```

| SEQ ID NO: 29 | moltype = DNA  length = 126 |
|---|---|
| FEATURE | Location/Qualifiers |
| source | 1..126<br>mol_type = other DNA<br>organism = synthetic construct |

SEQUENCE: 29
```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

| SEQ ID NO: 30 | moltype = DNA  length = 339 |
|---|---|
| FEATURE | Location/Qualifiers |
| source | 1..339<br>mol_type = other DNA<br>organism = synthetic construct |

SEQUENCE: 30
```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaa                          339
```

| SEQ ID NO: 31 | moltype = DNA  length = 741 |
|---|---|
| FEATURE | Location/Qualifiers |
| source | 1..741<br>mol_type = other DNA<br>organism = synthetic construct |

SEQUENCE: 31
```
caatctgccc tgactcagcc tgcctccgtg tctgggtctc ctggacagtc gatcaccatc    60
tcctgcactg gaaccagtag tgacgttggt ggttatgact atgtctcctg gtaccaacaa   120
cacccaggca aagcccccaa actcatgatt tatgatgtca gtaatcggcc ctcagggggtt   180
tctaatcgct tctctggctc caagtctggc aacacggcct ccctcaccat ctctgggctc   240
caggctgagg acgaggcgga ttattactgc agctcatatg caggcagcaa caatgtggta   300
ttcggcggag ggaccaagct gaccgtccta ggtggtggtg gttctggcgg cggcggctcc   360
ggaggtggtg gatcccaggt ccagctggtg cagtctgggg ctgaggtgaa gaagcctggg   420
tcctcggtga aggtctcctg caaggcttct ggaggcacct tcagcagcta tgctatcagc   480
tgggtgcgac aggcccctgg acaagggctt gagtggatgg gagggatcat ccctatcttt   540
ggtacagcaa actacgcaca gaagttccag ggcagagtca cgattaccgc ggacgaatcc   600
acgagcacag cctacatgga gctgagcagc ctgagatctg aggacacggc cgtgtattac   660
tgtgcgagag ggggagtagg agcagtacgt gggcatgctt ttgatatctg gggccaaggg   720
acaatggtca ccgtctcttc a                                             741
```

| SEQ ID NO: 32 | moltype = DNA  length = 1413 |
|---|---|
| FEATURE | Location/Qualifiers |
| source | 1..1413<br>mol_type = other DNA<br>organism = synthetic construct |

SEQUENCE: 32
```
caatctgccc tgactcagcc tgcctccgtg tctgggtctc ctggacagtc gatcaccatc    60
tcctgcactg gaaccagtag tgacgttggt ggttatgact atgtctcctg gtaccaacaa   120
cacccaggca aagcccccaa actcatgatt tatgatgtca gtaatcggcc ctcagggggtt   180
tctaatcgct tctctggctc caagtctggc aacacggcct ccctcaccat ctctgggctc   240
caggctgagg acgaggcgga ttattactgc agctcatatg caggcagcaa caatgtggta   300
ttcggcggag ggaccaagct gaccgtccta ggtggtggtg gttctggcgg cggcggctcc   360
ggaggtggtg gatcccaggt ccagctggtg cagtctgggg ctgaggtgaa gaagcctggg   420
tcctcggtga aggtctcctg caaggcttct ggaggcacct tcagcagcta tgctatcagc   480
tgggtgcgac aggcccctgg acaagggctt gagtggatgg gagggatcat ccctatcttt   540
ggtacagcaa actacgcaca gaagttccag ggcagagtca cgattaccgc ggacgaatcc   600
acgagcacag cctacatgga gctgagcagc ctgagatctg aggacacggc cgtgtattac   660
tgtgcgagag ggggagtagg agcagtacgt gggcatgctt ttgatatctg gggccaaggg   720
```

```
acaatggtca ccgtctcttc aaccacgacg ccagcgccgc gaccaccaac accggcgccc    780
accatcgcgt cgcagcccct gtccctgcgc ccagaggcgt gccggccagc ggcgggggc    840
gcagtgcaca cgagggggct ggacttcgcc tgtgatatct acatctgggc cccttggcc    900
gggacttgtg gggtccttct cctgtcactg gttatcaccc tttactgcaa acggggcaga    960
aagaaactcc tgtatatatt caaacaacca tttatgagca cagtacaaac tactcaagag   1020
gaagatggct gtagctgccg atttccagaa gaagaagaag gaggatgtga actgagagtg   1080
aagttcagca ggagcgcaga cgcccccgcg tacaagcagg ccagaaccca gctctataac   1140
gagctcaatc taggacgaag agaggagtac gatgttttgg acaagagacg tggccgggac   1200
cctgagatgg ggggaaagcc gagaaggaag aaccctcagg aaggcctgta caatgaactg   1260
cagaaagata agatggcgga ggcctacagt gagattgagt tgaaaggcga gcgccggagg   1320
ggcaaggggc acgatggcct ttaccagggt ctcagtacag ccaccaagga cacctacgac   1380
gcccttcaca tgcaggccct gccccctcgc taa                                1413

SEQ ID NO: 33          moltype = AA  length = 266
FEATURE                Location/Qualifiers
source                 1..266
                       mol_type = protein
                       organism = synthetic construct
SEQUENCE: 33
MDFQVQIFSF LLISASVIMS RGDIQMTQSP SSLSASVGDR VTITCRASQD VNTAVAWYQQ     60
KPGKAPKLLI YSASFLESGV PSRFSGSRSG TDFTLTISSL QPEDFATYYC QQHYTTPPTF    120
GQGTKVEIKR TGSTSGSGKP GSGEGSEVQL VESGGGLVQP GGSLRLSCAA SGFNIKDTYI    180
HWVRQAPGKG LEWVARIYPT NGYTRYADSV KGRFTISADT SKNTAYLQMN SLRAEDTAVY    240
YCSRWGGDGF VAMDVWGQGT LVTVSS                                        266

SEQ ID NO: 34          moltype = AA  length = 266
FEATURE                Location/Qualifiers
source                 1..266
                       mol_type = protein
                       organism = synthetic construct
SEQUENCE: 34
MDFQVQIFSF LLISASVIMS RGDIQMTQSP SSLSASVGDR VTITCRASQD VNTAVAWYQQ     60
KPGKAPKLLI YSASFLESGV PSRFSGSGSG TDFTLTISSL QPEDFATYYC QQHYTTPPTF    120
GQGTKVEIKR TGSTSGSGKP GSGEGSEVQL VESGGGLVQP GGSLRLSCAA SGFNIKDTYI    180
HWVRQAPGKG LEWVARIYPT NGYTRYADSV KGRFTISADT SKNTAYLQMN SLRAEDTAVY    240
YCSRWGGDGF VAMDVWGQGT LVTVSS                                        266

SEQ ID NO: 35          moltype = AA  length = 266
FEATURE                Location/Qualifiers
source                 1..266
                       mol_type = protein
                       organism = synthetic construct
SEQUENCE: 35
MDFQVQIFSF LLISASVIMS RGDIQMTQSP SSLSASVGDR VTITCRASQD VNTAVAWYQQ     60
KPGKAPKLLI YSASFLYSGV PSRFSGSRSG TDFTLTISSL QPEDFATYYC QQHYTTPPTF    120
GQGTKVEIKR TGSTSGSGKP GSGEGSEVQL VESGGGLVQP GGSLRLSCAA SGFNIKDTYI    180
HWVRQAPGKG LEWVARIYPT NGYTRYADSV KGRFTISADT SKNTAYLQMN SLRAEDTAVY    240
YCSRWGGDGF YAMDVWGQGT LVTVSS                                        266

SEQ ID NO: 36          moltype = DNA  length = 798
FEATURE                Location/Qualifiers
source                 1..798
                       mol_type = other DNA
                       organism = synthetic construct
SEQUENCE: 36
atggatttcc aggtccagat cttctcgttc ctcctgatct cggcttccgt gatcatgtcg     60
agaggcgaca tccagatgac ccagtcccca agttccctta gtgcctccgt cggggatcgc    120
gtgactatca cgtgcagggc atcccaggat gtgaacaccg ccgtggcctg gtaccagcag    180
aaacccggca aggcccccaa gctcctgatc tactctgcca gcttcttaga gagtggcgtc    240
ccctcccgct tctcgggcag tcgtagcggc accgacttca cactgaccat ctcgtccctg    300
cagccggagg actttgcaac ctactactgc cagcagcatt acacgacccc acctaccttc    360
ggccagggca ccaaggtgga gattaagcgc accggctcca ccagcggcag tggcaagccc    420
ggggagtggc agggttccga ggtccagctg gtggagtcag gcgggggcct ggtccaaccg    480
gggggttcgc tgaggctgag ctgcgctgca tccggcttca cactgaccat atatcaagga    540
cacttatatt
cattgggtgc ggcaagcccc agggaagggc ctggagtggg tcgcccgtat ctaccccact    600
aatggctaca ccaggtacgc ggattctgtg aaggggagat tcaccatttc ggcagacacc    660
tcgaagaata ccgcctacct gcaaatgaac tccctccgcg ctgaggacac tgccgtgtat    720
tactgtagtc gctggggcgg ggacgggttc gtggcaatgg acgtttgggg ccagggcacg    780
ctcgtgaccg tgtcctcc                                                 798

SEQ ID NO: 37          moltype = DNA  length = 798
FEATURE                Location/Qualifiers
source                 1..798
                       mol_type = other DNA
                       organism = synthetic construct
SEQUENCE: 37
atggatttcc aggtccagat cttctcgttc ctcctgatct cggcttccgt gatcatgtcg     60
agaggcgaca tccagatgac ccagtcccca agttccctta gtgcctccgt cggggatcgc    120
gtgactatca cgtgcagggc atcccaggat gtgaacaccg ccgtggcctg gtaccagcag    180
```

-continued

```
aaacccggca aggcccccaa gctcctgatc tactctgcca gcttcttaga gagtggcgtc 240
ccctcccgct tctcgggcag tggcagcggc accgacttca cactgaccat ctcgtccctg 300
cagccggagg actttgcaac ctactactgc cagcagcatt acacgacccc acctaccttc 360
ggccagggca ccaaggtgga gattaagcgc accggctcca ccagcggcag tggcaagccg 420
gggagtggcg agggttccga ggtccagctg gtggagtcag gggggggcct ggtccaaccg 480
gggggttcgc tgaggctgag ctgcgctgca tccggcttca atatcaagga cacttatatt 540
cattgggtgc ggcaagcccc agggaagggc ctggagtggg tcgcccgtat ctacccact 600
aatggctaca ccaggtacgc ggattctgtg aaggggagat tcaccatttc ggcagacacc 660
tcgaagaata ccgcctacct gcaaatgaac tccctccgcg ctgaggacac tgccgtgtat 720
tactgtagtc gctgggcgg ggacgggttc gtggcaatgg acgtttgggg ccagggcacg 780
ctcgtgaccg tgtcctcc                                              798

SEQ ID NO: 38          moltype = DNA  length = 798
FEATURE                Location/Qualifiers
source                 1..798
                       mol_type = other DNA
                       organism = synthetic construct
SEQUENCE: 38
atggacttcc aggtgcagat cttctccttc ttactgatct ccgcctcggt gatcatgagt 60
cgcggggaca tccagatgac acagtcgcca agttccctaa gcgccagtgt gggtgaccga 120
gtcaccatca cgtgtcgggc atcgcaggac gtgaacaccg cggtggcctg gtaccagcag 180
aagcccgaca aggccccaa gcttctgatc tactctgcat cctttctgta ctcgggcgtc 240
ccgtccaggt tctcgggatc ccggagtggg accgacttca ccctcaccat cagcagcctg 300
cagccagagg actttgctac ttactattgt cagcagcatt acacaactcc cccactttc 360
gggcagggca ccaaggtcga gattaagcgg acaggatcaa cgtccggcag tggcaagccc 420
ggaagcggca agggatccga ggtccagctg gtggagagtg gggggtggcct ggttcagcct 480
ggcggctcgc tgcgactgag ttgcgctgcc tccggcttca acatcaaaga cacgtacatt 540
cactgggtac gccaggcccc cggcaagggg ctggagtggg tcgcgcgcat ctacctaca 600
aacggctaca cgcggtatgc cgactctgtg aaaggacgct ttaccatttc ggccgacacc 660
tcgaagaaca cggcttatct ccagatgaac tccctgcgtg ctgaggatac cgcggtgtac 720
tactgctccc gctgggggagg cgacggcttc tacgccatgg atgtttgggg ccaaggcacc 780
cttgtgactg tgtcgagt                                              798
```